United States Patent [19]

Peterson et al.

[11] Patent Number: 5,402,361
[45] Date of Patent: Mar. 28, 1995

[54] APPARATUS FOR METHOD FOR LOGGING, STORING, AND REDIRECTION OF PROCESS RELATED NON-DENSITOMETRIC DATA GENERATED BY COLOR PROCESSING EQUIPMENT FOR USE BY AN OFF SITE HOST COMPUTER

[75] Inventors: Steven H. Peterson, Wyoming; Timothy R. Friend, Jenison, both of Mich.

[73] Assignee: X-Rite, Incorporated, Grandville, Mich.

[21] Appl. No.: 687,480

[22] Filed: Apr. 18, 1991

[51] Int. Cl.$^6$ .............................. G06F 3/00
[52] U.S. Cl. .................... 364/525; 395/200; 395/250; 355/204
[58] Field of Search ........... 364/525, 526, 413.07, 364/564, 571.01, 571.04, 55.01; 395/200, 250, 800; 370/61, 94.1; 355/203, 204, 205, 207, 208

[56] References Cited

U.S. PATENT DOCUMENTS

| | | | |
|---|---|---|---|
| 4,242,730 | 12/1980 | Golias et al. | 364/416 |
| 4,505,589 | 3/1985 | Ott et al. | 356/402 |
| 4,591,978 | 5/1986 | Peterson et al. | 395/325 |
| 4,654,794 | 3/1987 | O'Brien | 364/413.28 |
| 4,773,761 | 9/1988 | Sugiyama et al. | 356/405 |
| 4,780,744 | 10/1988 | Porter et al. | 355/208 |
| 4,959,771 | 9/1990 | Ardini, Jr. et al. | 395/250 |
| 5,015,098 | 5/1991 | Berg et al. | 356/402 |
| 5,020,055 | 5/1991 | May, Jr. | 370/94.1 |
| 5,062,714 | 11/1991 | Peterson et al. | 356/406 |
| 5,214,760 | 5/1993 | Hammond et al. | 395/250 |
| 5,237,566 | 8/1993 | Brand et al. | 370/61 |
| 5,291,420 | 3/1994 | Matsumoto et al. | 364/525 |

Primary Examiner—Eric Coleman
Assistant Examiner—L. Donaghue
Attorney, Agent, or Firm—Varnum, Riddering, Schmidt & Howlett

[57] ABSTRACT

A color measurement network message log structure is disclosed for use in controlling communications among systems such as a plurality of film processing laboratories and remotely located systems, including a remotely located host system. Each processing laboratory includes at least one film processing apparatus interconnected to a densitometer for obtaining data related to color quality during film processing procedures. Signals representative of color quality data are transmitted from the densitometer to the host system through conventional modem devices and telecommunication lines. The host system can comprise a conventional processor and interconnected printer device. The processor is responsive to signals received from the densitometer at each processing laboratory to process the color quality data represented thereby. Each of the densitometers is provided with a dual port structure for communications with the film processing apparatus and remotely located system. Signals representative of data from the film processing apparatus can be accepted by the densitometer, with the densitometer including a network message structure for queueing the data represented by the signals for purposes of subsequent transmission to the remotely located system. Signals representative of data can be received from the remotely located system and stored internally to the densitometer for purposes of subsequent transmission to a visual display or subsequent transmission to a peripheral device, such as a printer. Still further, the remotely located system is made capable of direct control of the film processing apparatus through the use of a pass-through mode associated with the dual port structure of the densitometer.

12 Claims, 25 Drawing Sheets

APPARATUS FOR METHOD FOR LOGGING, STORING, AND REDIRECTION OF PROCESS RELATED NON-DENSITOMETRIC DATA GENERATED BY COLOR PROCESSING EQUIPMENT FOR USE BY AN OFF SITE HOST COMPUTER

BACKGROUND OF THE INVENTION

1. Field of the Invention

The invention relates to apparatus and methods associated with color technology and, more particularly, to a communications structure for providing intercommunications among color measurement and processing apparatus, and remotely located systems.

2. Description of Related Art

It is well known that the term "color" as applied to electromagnetic radiation represents in part the relative energy distribution of radiation within the visible spectrum. That is, light providing a stimulus to the human eye, and having a particular energy distribution, may be perceived as a substantially different color than light of another energy distribution. Concepts relating to the characteristics of color and light waves are the subject of numerous well-known texts, such as *Principles of Color Technology*, Meyer, Jr. and Saltzman (Wiley 1966) and *The Measurement of Appearance*, Hunter and Harold (Wiley 2nd Ed. 1987).

In recent years, the capability of maintaining the "quality of color" has been of significant importance in various industries such as, for example, the fields of graphic arts, photography and color film processing. For purposes of performing sample testing and other activities in furtherance of maintaining color quality, it is necessary to first determine an appropriate means for "measuring" and "describing" color. A substantial amount of research has been performed during the past 50 years with respect to appropriate methods and standards for color measurement and description.

For purposes of describing color, and from a purely "physical" point of view, the production of color requires three things: a source of light; an object to be illuminated; and a means for perceiving the color of the object. The means for perceiving the color can be the human eye and brain or, alternatively, electrical and electromechanical apparatus such as a photosensitive detector and associated auxiliary devices utilized for detecting light. In general, it is desirable to provide a means for measuring color so as to assess the manner in which an image will appear to a human observer, or the manner in which an image will perform in a photographic or other type of reproduction printing operation.

Although human perception and interpretation of color can be useful, reliance on such perception and interpretation can be highly subjective. That is, human nature may cause one person's perception of the color of a particular object to be substantially different from the perception of another. In addition, eye fatigue, age and other physiological factors can influence color perception. Further, visual human perception is often insufficient for color description. For example, certain object samples may be visually perceived under one light source as substantially "matching", and yet may actually have very different spectral characteristics and may be perceived as "non-matching" under another light source. In view of the foregoing, it is desirable to employ color measurement and description techniques which are objective in nature, and capable of differentiating among object samples having different color characteristics.

Various devices have been developed and are widely utilized to measure and quantitatively describe color characteristics of object samples. Many of these devices provide measurements related to the spectral characteristics of the samples. Described simplistically, when light is directed onto an object sample to be measured for color, the object may absorb a portion of the light energy, while correspondingly passing through or reflecting (if the object is opaque) other portions of the light. The color characteristics of the object sample will depend in part on the spectral characteristics of the object. That is, the effect of an object on light can be described by its spectral transmittance or reflectance curves (for transparent or opaque materials, respectively). These spectral characteristic curves indicate the fraction of the source light at each wavelength transmitted by or reflected from the materials. Such curves are a means for describing the effect of an object on light in a manner similar to the use of a spectral energy distribution curve for describing the characteristics of a source of light. Instruments utilized for generating such spectral characteristic curves are typically referred to as spectrophotometers.

In accordance with conventional optical physics, it is known that the proportion of light incident to an object sample and absorbed by such a sample is independent of the light intensity. Accordingly, a quantitative indication of the spectral characteristics of an object sample can be defined as the "transmittance" or "reflectance" of the sample. That is, the transmittance of a substantially transparent object can be defined as the ratio of power transmitted over light power incident to the sample. Correspondingly, for an opaque object sample, the reflectance can be defined as the ratio of power reflected from the object over the incident light power.

For collimated light, these ratios can be expressed in terms of intensities, rather than power. Furthermore, because of the nature of transmittance/reflectance and the optical characteristics of the human eye, it is advantageous to express these ratios in logarithmic form. Accordingly, one parameter widely used in the field of color technology for obtaining a quantitative measurement or "figure of merit" is typically characterized as optical "density." The optical density of an object sample is typically defined as follows:

$$\text{Optical Density} = D = -\log_{10} T \text{ or } -\log_{10} R \quad \text{(Equation 1)}$$

where T represents transmittance of a transparent object and R represents reflectance of an opaque object. In accordance with the foregoing, if an object sample absorbed 90% of the light incident upon the sample, and the object were opaque, the reflectance would ideally be 10%. The density of such a sample would then be characterized as unity. Correspondingly, if 99.9% of the light were absorbed, the reflectance would be 0.1% and the density would be 3. Similarly, the density of an "ideal" object reflecting 100% of the light incident upon the object would be 0.

To provide a relative measurement of color, it is possible to utilize the principles of optical density, without requiring measurement or knowledge of the absolute values of total incident light intensity or reflectance. That is, for example, it is possible to obtain relative color measurements among a series of object samples by utilizing a particular geometric configuration of light, object sample and reflectance or transmittance detector for each measurement, and standardizing the measurements in some desired manner.

In brief summary, optical density is a measurement of the modulation of light or other radiant flux by an object sample, such as a given area of a photographic print. Density measurements provide a means to assess the manner in which an image will appear to a human observer, or the way an image will perform in a film processing operation. Density measurements can be utilized to produce sensitometric curves to evaluate various printing and reproduction characteristics, as well as utilization to control various photographic operations, such as film processing.

For purposes of measuring optical densities, it is well known to employ a device typically characterized as a "densitometer." These densitometers are often categorized as either "reflection" densitometers, employed for optical density measurements of opaque objects, or are otherwise characterized as "transmittance" densitometers. Transmittance densitometers are employed for determining spectral characteristics of various nonopaque materials.

Densitometers are utilized in various industries for performing a variety of functions. For example, densitometers can be conveniently employed in color film processing applications. Processes associated with these applications will be described in greater detail in subsequent paragraphs herein.

To assist in describing the principles of densitometer apparatus in which concepts of the present invention may be employed, FIG. 1 illustrates a simplified schematic representation of a known reflection densitometer configuration 100. A configuration of this type is described in detail in the commonly assigned and currently pending U.S. Patent application Ser. No. 534,205, filed Jun. 7, 1990, which is a continuation of commonly assigned U.S. Patent application Ser. No. 105,424 filed Oct. 5, 1987 and now abandoned. Densitometer apparatus of the type shown in FIG. 1 are characterized as reflection densitometers, and utilized to provide color density measurements of opaque materials as previously described.

Referring specifically to FIG. 1, and to numerical references therein, the densitometer apparatus 100 includes a light source unit 102 having a source light 104. With respect to optical density measurements in photography, color film processing, and other industrial fields, various standards have been developed for densitometer light source illuminants. For example, densitometer light source standards have previously been described in terms of a tungsten lamp providing an influx from a lamp operating at a Planckian distribution of 3000° K. Other suggested standards have been developed by the American National Standards Institute ("ANSI") and the International Organization for Standardization ("ISO"). These source light densitometer standards are typically defined in terms of the spectral energy distribution of the illuminant. The source light 104 preferably conforms to an appropriate standard and can, for example, comprise a filament bulb meeting a standard conventionally known in the industry as 2856K ANSI. Power for the source light 104 and other elements of the densitometer apparatus 100 can be provided by means of conventional rechargeable batteries or, alternatively, interconnection to AC utility power.

The source light 104 projects light through a collimating lens 106 which serves to focus the electromagnetic radiation from the source light 104 into a narrow collimated beam of light rays. Various types of conventional and well-known collimating lenses can be employed. The light rays transmitted through the collimating lens 106 project through an aperture 108. The dimensions of the aperture 108 will determine the size of the irradiated area of the object sample under test.

Various standards have been defined for preferable sizes of the irradiated area. Ideally, the aperture 108 is of a size such that the irradiance is uniform over the entire irradiated area. However, in any physically realizable densitometer arrangement, such uniform irradiance cannot be achieved. Current standards suggest that the size of the irradiated area should be such that irradiance measured at any point within the area is at least 90% of the maximum value. In addition, however, aperture size is typically limited to the size of the color bar or color patch area to be measured, and is also sized so as to reduce stray light.

The light rays emerging from the aperture 108 (illustrated as rays 110 in FIG. 1) are projected onto the irradiated area surface of an object sample 112 under test. The sample 112 may be any of numerous types of colored opaque materials. For example, in the printing industry, the sample 112 may be an ink-on-paper sample comprising a portion of a color bar at the edge of a color printing sheet. Further, with respect to the illustrative embodiment of a densitometer apparatus employing the principles of the invention as described in subsequent paragraphs herein, the sample 112 may be a control strip employed in the color film processing industry.

As the light rays 110 are projected onto the object sample 112, electromagnetic radiation shown as light rays 114 will be reflected from the sample 112. Standard detection configurations have been developed, whereby reflected light is detected at a specific angle relative to the illumination light rays 110 projected normal to the plane of the object sample 112. More specifically, standards have been developed for detection of reflected light rays at an angle of 45° to the normal direction of the light rays 110. This angle of 45° has become a standard for reflectance measurements, and is considered desirable in that this configuration will tend to maximize the density range of the measurements. In addition, however, the 45° differential also represents somewhat of a relatively normal viewing configuration of a human observer (i.e. illumination at a 45° angle from the viewer's line of sight).

For purposes of providing light detection, a spectral filter apparatus 116 is provided. The filter apparatus 116 can include a series of filters 118, 120 and 122. The filters 118, 120 and 122 are employed for purposes of discriminating the cyan, magenta and yellow spectral responses, respectively. That is, each of the filters will tend to absorb light energy at frequencies outside of the bandwidth representative of the particular color hue of the filter. For example, the cyan filter 118 will tend to absorb all light rays, except for those within the spectral bandwidth corresponding to a red hue. By detecting reflected light rays only within a particular color hue bandwidth, and obtaining an optical density measurement with respect to the same, a "figure of merit" can be obtained with respect to the quality of the object sample coloring associated with that particular color hue.

It is apparent from the foregoing that the actual quantitative measurement of color density or color reflectance is dependent in substantial part on the spectral transmittance characteristics of the filters. Accordingly, various well-known standards have been developed with respect to spectral characteristics of densitometer filters. For example, one standard for densitometer filters is known as the ANSI status T color response. The spectral response characteristics of filters meeting this standard are relatively wide band (in the range of 50–60 namometers (nms) bandwidth) for each of the cyan, magenta and yellow color hues. Other spectral response characteristic standards include, for example, what is known as G-response, which is somewhat similar to status T, but is somewhat more sensitive with respect to yellow hues. An E-response represents a European response standard.

Although the filters 118, 120 and 122 are illustrated in the embodiment shown in FIG. 1 as the cyan, magenta and yellow color shades, other color shades can clearly be employed. These particular shades are considered somewhat preferable in view of their relative permanence, and because they comprise the preferred shades for use in reflection densitometer calibration. However, it is apparent that different shades of red, blue and yellow, as well as entirely different colors, can be utilized with the densitometer apparatus 100.

The spectral filters 118, 120 and 122 may not only comprise various shades of color, but can also be one of a number of several specific types of spectral response filters. For example, the filters can comprise a series of conventional Wratten gelatin filters and infrared glass. However, various other types of filter arrangements can also be employed.

The spectral filters 118, 120 and 122 are preferably positioned at a 45° angle relative to the normal direction from the plane of the object sample 112 under test. In the particular example shown in FIG. 1, each of these filters is maintained stationary and utilized to simultaneously receive light rays reflected from the object sample 112. Further, although the particular example illustrated in FIG. 1 may include a stationary object sample 112, the example embodiment of a densitometer apparatus employing principles of the invention as described in subsequent paragraphs herein can include an object sample which is continuously moving relative to the spectral filter arrangement. In such an instance, the actual spectral filter measurements may be obtained simultaneously or, alternatively, in sequence.

As further shown in FIG. 1, the portion of the reflected light rays 114 passing through the filters 118, 120 and 122 (shown as light rays 124, 126 and 128, respectively) impinge on receptor surfaces of photovoltaic sensor cells. The sensor cells are illustrated in FIG. 1 as sensors 132, 134 and 136 associated with the spectral filters 124, 126 and 128, respectively. The sensors 132, 134 and 136 can comprise conventional photoelectric elements adapted to detect light rays emanating through the corresponding spectral filters. The sensors are further adapted to generate electrical currents having magnitudes proportional to the intensities of the sensed light rays. As illustrated in FIG. 1, electrical current generated by the cyan sensor 132 in response to the detection of light rays projecting through the filter 118 is generated on line pair 138. Correspondingly, electrical current generated by the magenta sensor 134 is applied to the line pair 140, while the electrical current generated by the yellow sensor 136 is applied as output current on line pair 142. Photoelectric elements suitable for use as sensors 136, 138 and 140 are well-known in the art, and various types of commercially-available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral reflectance curve of the object sample 112, and the spectral response curve of the corresponding filter. Accordingly, for a particular color shade represented by the spectral response curve of the filter, the magnitude of the electrical current represents a quantitative measurement of the proportional reflectance of the object sample 112 within the frequency spectrum of the color shade.

As further shown in FIG. 1, the sensor current output on each of the line pairs 138, 140 and 142 can be applied as an input signal to one of three conventional amplifiers 144, 146 and 148. The amplifier 144 is responsive to the current output of cyan sensor 132 on line pair 138, while amplifier 146 is responsive to the sensor current output from magenta sensor 134 on line pair 144. Correspondingly, the amplifier 148 is responsive to the sensor current output from yellow sensor 136 on line pair 142. Each of the amplifiers 144, 146 and 148 provides a means for converting low level output current from the respective sensors on the corresponding line pairs to voltage level signals on conductors 150, 152 and 154, respectively. The voltage levels of the signals on their respective conductors are of a magnitude suitable for subsequent analog-to-digital (A/D) conversion functions. Such amplifiers are well known in the circuit design art, and are commercially available with an appropriate volts per ampere conversion ratio, bandwidth and output voltage range. The magnitudes of the output voltages on lines 150, 152 and 154 again represent the intensities of reflected light rays transmitted through the corresponding spectral filters.

Each of the voltage signal outputs from the amplifiers can be applied as an input signal to a conventional multiplexer 156. The multiplexer 156 operates so as to time multiplex the output signals from each of the amplifiers 144, 146 and 148 onto the conductive path 158. Timing for operation of the multiplexer 156 can be provided by means of clock signals from master clock 160 on conductive path 162. During an actual density measurement of an object sample, the densitometer 100 will utilize a segment of the resultant multiplexed signal which sequentially represents a voltage output signal from each of the amplifiers 144, 146 and 148.

The resultant multiplexed signal generated on the conductive path 158 is applied as an input signal to a conventional A/D converter 164. The A/D converter 164 comprises a means for converting the analog multiplexed signal on conductor 158 to a digital signal for purposes of subsequent processing by central processing unit (CPU) 166. The A/D converter 164 is preferably controlled by means of clock pulses applied on conductor 168 from the master clock 160. The clock pulses operate as "start" pulses for performance of the A/D conversion. The A/D converter 164 can be any suitable analog-to-digital circuit well known in the art and can, for example, comprise 16 binary information bits, thereby providing a resolution of 65K levels per input signal.

The digital output signal from the A/D converter 164 can be applied as a parallel set of binary information bits on conductive paths 170 to the CPU 166. The CPU 166 can provide several functions associated with operation of the densitometer apparatus 100. In the embodiment described herein, the CPU 166 can be utilized to perform these functions by means of digital processing and computer programs. In addition, the CPU 166 can be under control of clock pulses generated from the master clock 160 on path 172. However, a number of the functional operations of CPU 166 could also be provided by means of discrete hardware components.

In part, the CPU 166 can be utilized to process information contained in the digital signals from the conductive paths 170. Certain of this processed information can be generated as output signals on conductive path 176 and applied as input signals to a conventional display circuit 178. The display circuit 178 provides a means for visual display of information to the user, and can be in the form of any one of several well-known and commercially-available display units.

In addition to the CPU 166 receiving digital information signals from the conductive paths 170, information signals can also be manually input and applied to the CPU 166 by means of a manually-accessible keyboard circuit 180. The user can supply "adjustments" to color responses by means of entering information through the keyboard 180. Signals representative of the manual input from the keyboard 180 are applied as digital information signals to the CPU 166 by means of conductive path 182.

The previously described concepts of densitometry can be of primary significance in fields such as the color photography and processing industry. For purposes of illustration and example, the color photograph processing procedure can be described as comprising a series of three process steps. First, the exposed roll or strip of color film is subjected to a process for producing a series of "negatives" from the exposed film roll or strip. This process is well known in the photography industry and can essentially be characterized as a chemical process for producing a series of negative images, in which the "brightness" values of the photograph subject are reproduced so that the lightest areas are shown as the darkest areas.

Secondly, the color photography development process comprises a step wherein the photographic negative is utilized with photographic paper in a manner such that the photographic paper is subjected to exposure from the negative. In this process, the film base and exposure times can be varied as appropriate to achieve the proper color balance on the exposed paper. Finally, the exposed film paper is subjected to a chemical process for generating the finished photographic prints.

Each of the aforedescribed processes is relatively conventional and well known in the photographic industry. However, each of these processes requires the "setting" of various control variables on the equipment utilized to perform the processes. For example, the processes associated with producing the negatives and processing the exposed paper comprise chemical processes whereby color chemistry variables may be adjusted so as to produce negatives and finished prints of appropriate colors. Correspondingly, the process step whereby the photographic print paper is exposed from the negatives will also have various variables associated with the process. For example, this particular process will involve the use of "white" light sources and spectral filters for exposing the negative onto the photographic paper in differing manners. Further, a variable associated with this particular process comprises the exposure times for the exposure of the negative onto the photographic paper. As an example, the negative may be exposed onto the paper through an unfiltered white light source for a certain predetermined period of time. However, if such an exposure is not producing an appropriate color balance, filters may be employed whereby only a particular color (i.e. energy from a portion of the color spectrum) of the white light source is exposed onto the photographic paper for some portion of the entirety of the exposure time. This type of operation is typically referred to as a "balancing" of the color.

With respect to the final step of the photographic development process, i.e. the processing of the exposed photographic paper to produce the final photographic prints, a number of variables are also associated with this type of process. For example, the chemistry of the film bath may be varied through the use of various chemical mixtures so to again achieve correct print processing to maintain appropriate photograph colors.

Various methods and equipment have been developed for providing the photograph developers with a means for measuring the "quality" of the individual process steps associated with the entirety of the photograph development process. In particular, it is relatively well known to utilize densitometers to measure optical transmittance density of processed negatives and optical reflectance density of processed photographic paper to determine if the equipment is producing appropriate color balances. However, when measuring color densities to determine the quality of the film processing, it is desirable to compare such density measurements against "ideal" processed materials. Accordingly, the field of film processing readily lends itself to the comparison of color densities of materials processed by the operator's own equipment against reference standards.

Further, however, the photographic industry does not have any ideal standards related to each of the process steps associated with film development. Additionally, optimum color densities of processed materials may vary dependent upon the particular type of film or paper material being utilized by the operator. Accordingly, manufactures of film processing equipment and materials will provide their own individual reference standards for purposes of optimizing the film development process.

More specifically, it is known in the field of color photograph film processing to utilize "strips" of negative and paper materials to periodically test the quality of the operator's own processing equipment. In addition, manufacturers also provide "reference" strips of materials which can be characterized as processed strips comprising "ideal" processing of the manufacturers' materials.

To further illustrate the use of the reference strips and the control strips, a strip commonly identified as the Kodak C-41 strip is illustrated in FIG. 2. The C-41 strip is manufactured by Eastman Kodak Company. The strip illustrated in FIG. 2 is identified as strip 200 and comprises a film negative having various color hues associated with the negative. When the film development equipment operator is utilizing film negatives manufactured by Eastman Kodak, the operator will obtain a referenced film strip and a series of control strips having a configuration as shown in FIG. 2. The reference strip can be characterized as a negative which has been fully processed by the manufacturer. The negative is considered to comprise a series of color patches having the "ideal" color hues for the negative processing. Correspondingly, the control strips provided by the manufacturer will be a series of unprocessed strip negatives. The principal use and concept associated with these strips is to allow the operator to adjust the film negative processor so that the color densities of control strips processed by the negative processor will optimally "match" color densities of the reference strip.

To perform the operation of measuring the quality of the negative processing, a densitometer can first be used to measure the transmission densities of the reference strip. Again, these transmission densities represent ideal densities to be achieved by the equipment negative processor. Although it would be possible to utilize color density values somehow identified on the reference strip, such values may not comprise the same density values which will be measured by the operator's own densitometer. That is, the "absolute values" of the color densities are not particularly important. Instead, the quality of the film negative processing by the operator's equipment will be indicated by the comparison of the measured color densities of a processed control strip relative to the measured color densities of the reference strip. Because densitometers may vary in their measurement readings from one device to another, it is of primary importance that the color densities for the reference strip and the control strips be measured by the same device.

After measurement of the color densities associated with the reference strip, a control strip having a similar configuration to the strip 200 is processed by the operator, using the operator's own equipment. Following processing of the film negative, the processed control strip is now measured to determine the color densities associated therewith. The differences in the relative color density measurement values between the reference strip and the processed control strip will indicate to the operator whether any adjustments in the film negative processing operation are required. Indeed, many of the primary manufacturers will provide written "trouble shooting" manuals indicating the types of adjustments which may be necessary in view of certain types of differences between the density measurements associated with the processed control strip and the density measurements associated with the reference strip. As an example, the operator may find that the "green" density value for the processed control strips is continuously lower than the green density value for the reference strip. The written trouble shooting manuals may then provide suggestions as to the particular activities which may be undertaken by the operator with respect to adjustment of the negative processor equipment.

With respect to adjustments to the processing equipment associated with the exposure of the negative onto the photographic paper, manufacturers provide reference and control strips commonly known as "print balance" strips. Such a print balance control strip is illustrated in FIG. 3 as print balance strip 202. As shown in FIG. 3, the strip comprises three color patches identified as the "over", "normal" and "under" patches These patches comprise color densities which may be expected with respect to photographic paper that has been overexposed, normal and underexposed, respectively. The print balance control strips are employed to maintain a printing balance during the exposure of a negative onto the photographic paper. Again, in a manner similar to the processing step associated with processing the negative, the manufacturers will provide a print balance reference strip, in addition to a series of unprocessed print balance strips. The operator would again measure the color densities of the patches of the reference strip representative of overexposure, normal processing and underexposure. These color density values would then be compared against the actual color density values of materials processed by the operator's own equipment. These measurements can assist the operator in adjusting exposure times and filtering so as to achieve a proper color balance in exposing the negative onto the photographic paper.

With respect to the third step of the overall development process, i.e. the processing of the exposed photographic paper to obtain the final photographic prints, the manufacturers provide further reference and control strips to adjust variables in the processing step. A control strip commonly identified as the Kodak EP-2 strip (manufactured by the Eastman Kodak Company) is illustrated as control strip 204 in FIG. 4. Again, the operator would be provided with the reference strip having the "ideal" color densities. That is, the reference strip would comprise a strip of photographic prints having the ideal color densities for this processing step. The operator would measure these reflection color densities and compare the densities against control strips processed by the operator's own equipment. Manufacturers provide written trouble shooting manuals for this processing step in a manner similar to the materials provided for the production of the film negatives. That is, differences in the measured color densities will typically indicate certain problems associated with this step of the film processing. As an example, a relatively substantial distinction in the color densities of particular color patches between a processed control strip and the reference strip may indicate that the bath temperature for the processing of the final photographic print is not appropriate.

A substantial advance has been achieved in the art of densitometer development with an automated strip reader densitometer. This automated strip reader densitometer is disclosed in the commonly assigned and currently pending U.S. Patent application Ser. No. 480,331, filed Feb. 13, 1990, which is a continuation of commonly assigned U.S. Patent application Ser. No. 309,342, filed Feb. 10, 1989, and now abandoned. The '331 patent application is hereby incorporated by reference herein, and is subsequently referred to herein as the Cargill et al application. With the automated strip reader densitometer, control strips are essentially read "on the fly" as the control strips pass through various elements of the densitometer.

Densitometers of the type previously described herein can be employed within a network structure comprising a plurality of film processing laboratories, along with a remotely located host computer processing system. Each processing laboratory may include one or more film processing apparatus interconnected to the densitometer for purposes of obtaining data related to color quality during film processing procedures. Further, it is also known to essentially control the processor of the densitometer through commands executed from and transmitted to the densitometer via conventional telecommunications lines and conventional modem devices. The concept of intercommunications between a densitometer of the type described herein and a peripheral device such as a separate computer processor is disclosed in detail in commonly assigned U.S. Pat. No. 4,591,978 issued to Peterson et al on May 27, 1986. The disclosure of the Peterson et al patent is hereby incorporated herein by reference.

It is also known to employ communication arrangements which allow the collection and visual display of film processing laboratory data, and for purposes of generally creating and managing data transmitted to film processing laboratories from remotely located host computer processors. However, such communications arrangements have, to date, been somewhat inefficient with respect to general operation. For example, such arrangements have been somewhat device dependent with respect to data received by the densitometer from other devices. That is, a relatively "fixed" format for such data has been required with respect to the types of data received, message formats and the like.

SUMMARY OF THE INVENTION

In accordance with the invention, a method is provided for use within a communications network arrangement having a plurality of processing laboratories. Each of the processing laboratories includes at least one densitometer and film or paper processing apparatus. The network arrangement also includes a host system remotely located from the processing laboratories. Means are provided for establishing data communications between the processing laboratories and the host system.

The method provides for data transmission between one of the processing laboratories and the host system. The method includes establishing a telecommunications connection between the processing laboratory and the host system. A set of signals is serially transmitted from the host system which is indicative of data to be stored within the densitometer of the processing laboratory. A memory block as a log buffer memory is reserved within a memory of the densitometer. The data signals are received at the densitometer and sequentially stored within the log buffer memory.

Each of the received data signals is interrogated so as to determine when and if a signal indicative of termination has occurred. Storage of the data signals ceases upon receipt of the signal indicative of termination. Along with the data signals stored within the log buffer memory, additional data signals are also stored indicative of a date and time when the data signals were received from the processing laboratory.

In accordance with the invention, an apparatus is provided for use in a film or paper processing laboratory. The apparatus is connected for communications to a host system remotely located from the processing laboratory. The apparatus includes a densitometer having light source means for projecting light toward a colored surface of an object sample under test at an angle of illumination relative to the surface. Light receiving means are provided for receiving light rays reflected from the object sample under test at a reflection angle relative to the object sample surface.

Detection means are provided within the densitometer. The detection means are connected to the light receiving means for detecting light rays reflected from the object sample surface and for generating electrical signals representative of spectral characteristics of the object sample surface. Processing means are provided within the densitometer which are connected to the detection means and responsive to the electrical signals for generating data representative of the spectral characteristics.

In addition, and in accordance with the invention, a memory structure is provided of predetermined length having a plurality of data storage locations of predetermined number for storing data received from and transmitted to the other apparatus within the processing laboratory and the host system. The data is stored as a series of data blocks of variable length, with each of the data blocks having a first set of data identifying a time of storage of the corresponding data block in the memory structure.

Means are also provided for generating and storing the time of storage of the corresponding data block. At least one secondary port means is provided for receiving data from the other apparatus within the processing laboratory, and for storing the received data in the data blocks. At least one primary port means is provided for transmitting data stored in the data blocks to the host system.

The processing means includes means for transmitting the series of data blocks received from the other apparatus to the host system through the primary port means in a format consistent with the format in which the data blocks are received from the other apparatus. This transmission occurs without the apparatus performing any modifications to the format of the data blocks as received from the other apparatus. Further, the apparatus does not require an independent or dedicated processor for performing or monitoring communications or control functions associated with transmission of data between the other apparatus within the processing laboratory and the host system.

The secondary port means is further adapted for transmitting data stored in the data blocks to the other apparatus within the processing laboratory. In addition, the primary port means is adapted for receiving data from the host system and for storing received data in the data blocks. Means are provided for switching the secondary and primary port means into states whereby data received from the host system at the secondary port means is passed to the other apparatus within the processing laboratory through the secondary port means, without necessitating storage of data in the memory structure.

Means are also provided for switching the secondary and the primary port means into states whereby data received from the other apparatus within the processing laboratory at the secondary port means is passed to the host system through the primary port means without necessitating storage of the data in the memory structure.

The apparatus further includes means for interrogating data signals representative of data to be stored in the memory structure and transmitted from the other apparatus within the processing laboratory, so as to determine when and if a data signal indicative of termination has been received. Means are also provided for ceasing storage of the data in the memory structure representative of the data signals, upon receipt of the data signal indicative of termination. Further, an indicating means is provided for receiving a data signal from the other apparatus through the secondary port means, within the indicating data signal being indicative of the specific data signal being considered as indicative of termination during subsequent receipt of data signals from the other apparatus through the secondary port means.

The apparatus also includes displays means for displaying information to a user of the densitometer apparatus. Means are also provided for transmitting data stored within the memory structure to the display means. In accordance with one aspect of the invention, the secondary port means includes four serial ports.

The apparatus also includes means responsive to specific data received through the secondary port means from the other apparatus within the processing laboratory for storing subsequently received data in the memory structure. The specific data comprises data representative of an instruction command for instructing the apparatus to enter the subsequently received data in the memory structure, and also comprises data representative of an expected termination character. Means are provided for determining when and if any of the subsequently received data corresponds to the termination character. In addition, means are also provided for ceasing storage of the subsequently received data in the event of receipt of data corresponding to the termination character.

The apparatus also includes means responsive to user input for storing data indicative of an expected termination character or a time-out period. Means are further provided for storing data indicating the data subsequently received through the secondary port means from the other apparatus is to be stored in the memory structure until receipt of data corresponding to the expected termination character or until a period of time corresponding to the time-out period has elapsed. The subsequently received data is stored in the memory structure from the other apparatus without the requirement of the apparatus receiving an instruction command from the other apparatus for instructing the apparatus to enter the subsequent received data into the memory structure.

The apparatus also includes means responsive to user input for storing data indicative of an expected termination character or a time-out period corresponding to an elapsed period of time. Means are further provided which are responsive to user input for storing data indicating the data subsequently received through the secondary port means from the other apparatus is to be stored in the memory structure until receipt of data corresponding to the expected termination character, or until a period of time corresponding to the time-out period has elapsed.

The apparatus also includes light receiving means for receiving light rays transmitted through the object sample under test at a transmission angle relative to the object sample surface. Detection means are provided within the densitometer and are connected to the light receiving means for detecting the light rays transmitted through the object sample surface. The detection means generates electrical signals representative of spectral characteristics of the object sample surface. In addition, means are provided for detecting an abnormal operating condition. Further means are responsive to the detection of the abnormal operating condition for storing data within the memory structure indicative of the abnormal operating condition. Means are further provided for transmitting the stored data representative of the abnormal operating condition through the primary port means to the host system.

BRIEF DESCRIPTION OF THE DRAWINGS

The invention will now be described with respect to the drawings, in which.

DESCRIPTION OF THE PREFERRED EMBODIMENT

Figure 5:
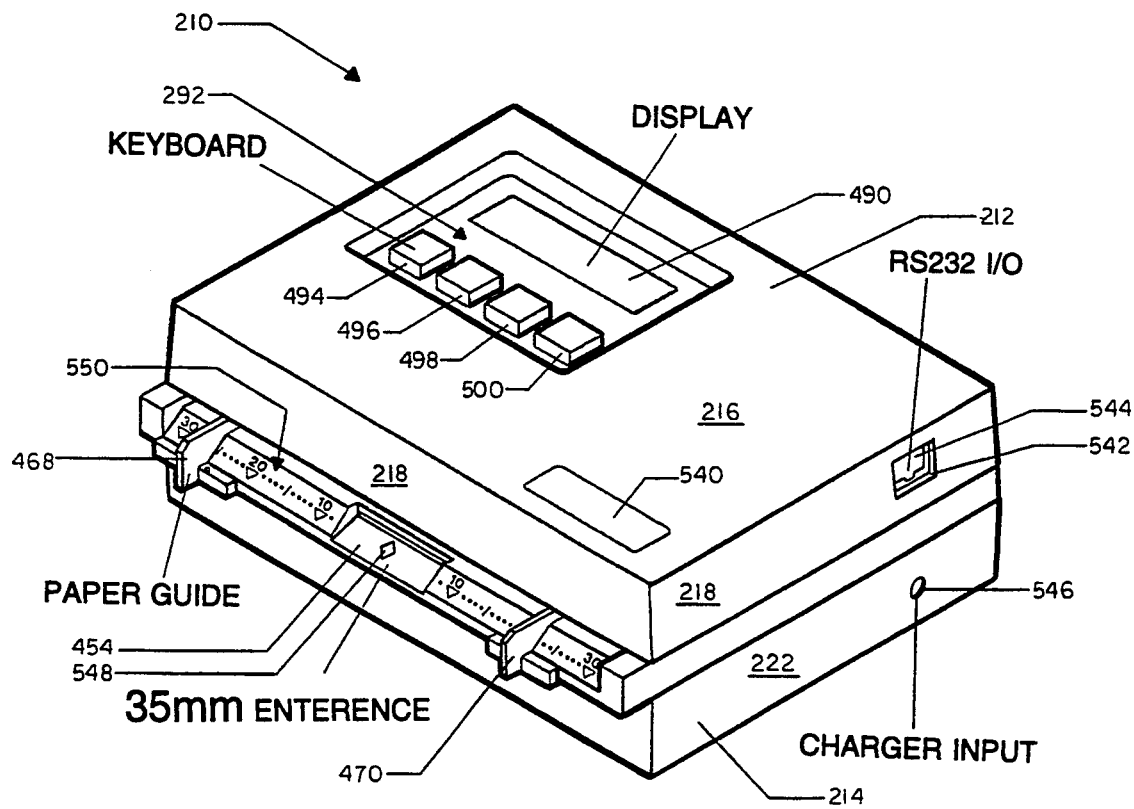
FIG. 5 is a perspective view of a densitometer apparatus which can be utilized in accordance with the invention.

The principles of the invention relate to a message buffer structure for use with color measurement devices and associated apparatus and are disclosed, by way of example, for use with a densitometer apparatus such as the densitometer apparatus 210 illustrated in FIG. 5. The densitometer apparatus 210 comprises an automated strip reader color photographic densitometer, whereby film control strips, paper control strips and printer balance strips can be inserted for motorized and automatic measurements. In particular, the densitometer apparatus 210 is adapted to measure a plurality of different types of manufacturers' control strips, and sort data for measured fields, such as high density, low density and "stain." In addition, the densitometer apparatus 210 is adapted to display the data and, if desired by the operator, transmit the data to a peripheral device, such as a printer. A detailed description of the mechanical and electrical elements of the densitometer apparatus 210 are set forth in the disclosure of the Cargill et al application.

The densitometer apparatus 210 can provide an output of red, blue and green color density values for each measured field of a control strip. However, it will be apparent to those skilled in the appropriate arts that various other color density outputs could be achieved without departing from the principal concepts of the invention disclosed and claimed in the Cargill et al application. As also disclosed in the Cargill et al application, the densitometer apparatus 210 is adapted to measure both optical transmission densities (for film negatives) and optical reflection densities (for photographic paper) of the control strips. In addition, the densitometer apparatus 210 is also adapted to provide color density measurements of data aligned adjacent edges of a control strip or, alternatively, at the center of a control strip. Still further, the densitometer apparatus 210 is further adapted to provide automatic calibration for transmission and reflection densitometry.

The physical structure of the densitometer apparatus 210 is simply illustrated in FIG. 5. As previously described, details of the densitometer apparatus 210 are set forth in the Cargill et al application. Referring specifically to FIG. 5, the apparatus 210 comprises a relative compact structure suitable for use on a desk top or similar work surface. The apparatus 210 includes a top cover 212 and a bottom cover 214. The top cover 212 comprises an upper surface 216 having a rectangular configuration and integral with downwardly extending side surfaces 218 at the edges thereof. The bottom cover 214 comprises a lower and rectangular flat surface having outwardly extending side surfaces 222 integral with the flat surface.

Figure 7:
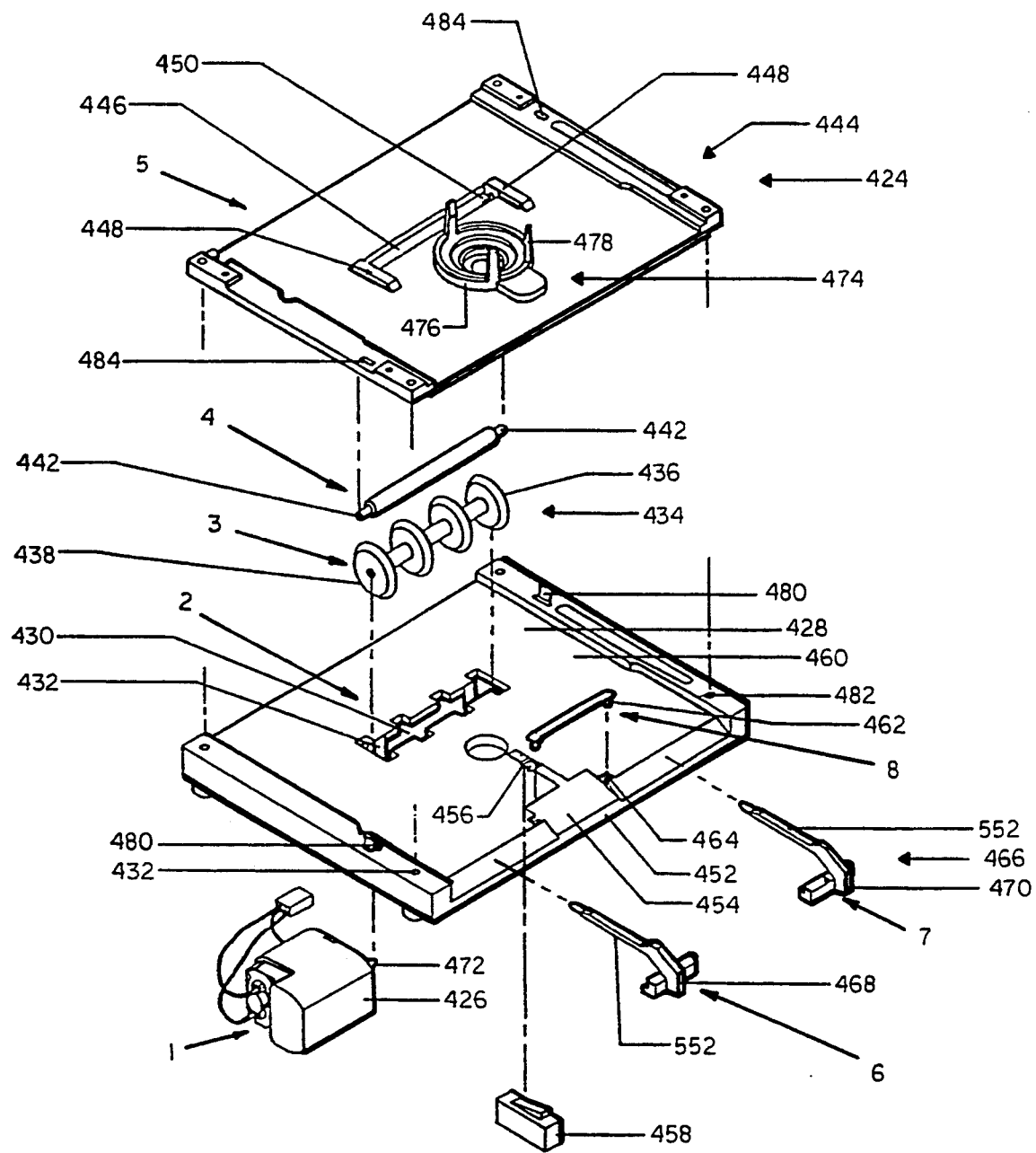
FIG. 7 is an exploded view of the densitometer apparatus shown in FIG. 6, and further showing the drive assembly for the apparatus.
Figure 8:
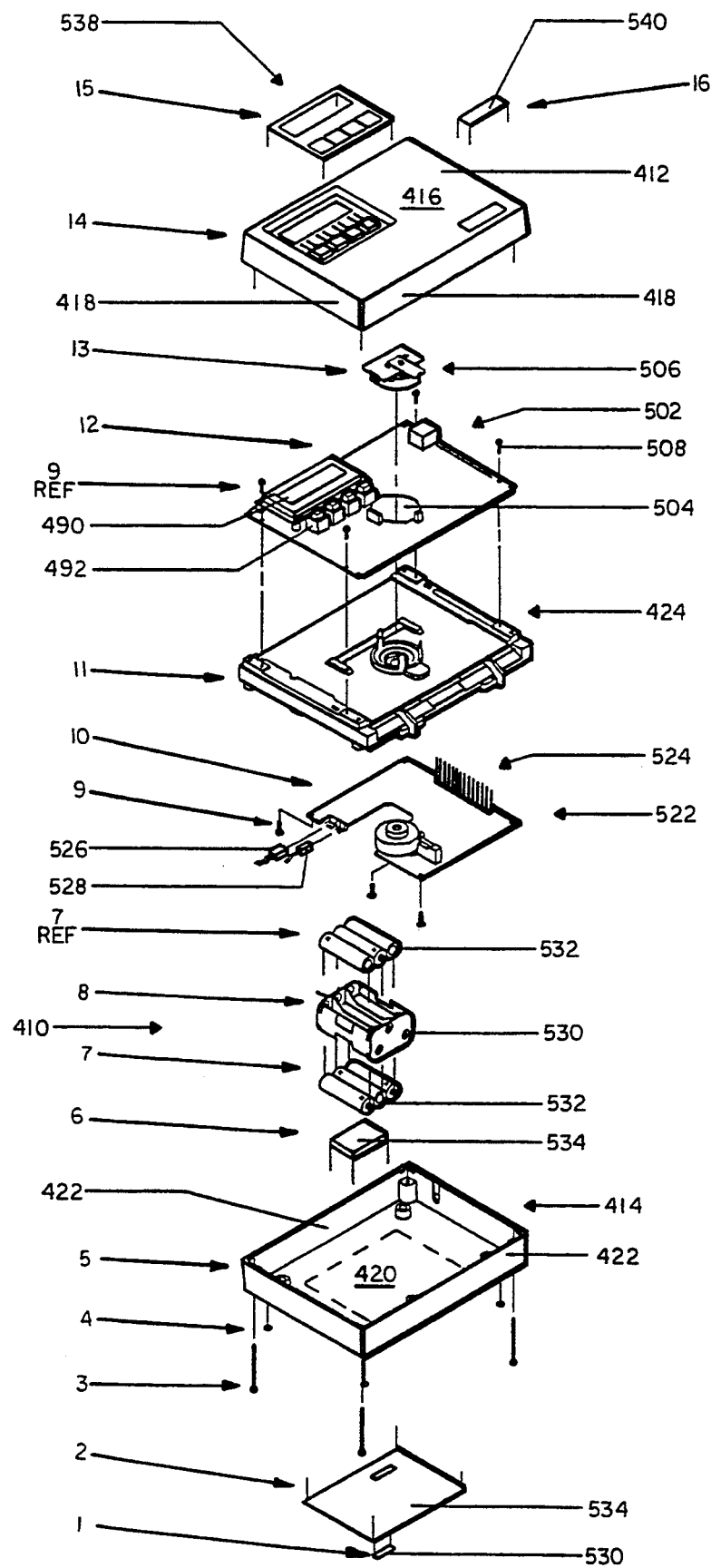
FIG. 8 is an exploded view of the apparatus shown in FIG. 5, and further showing various individual components of the apparatus.
Figure 9:
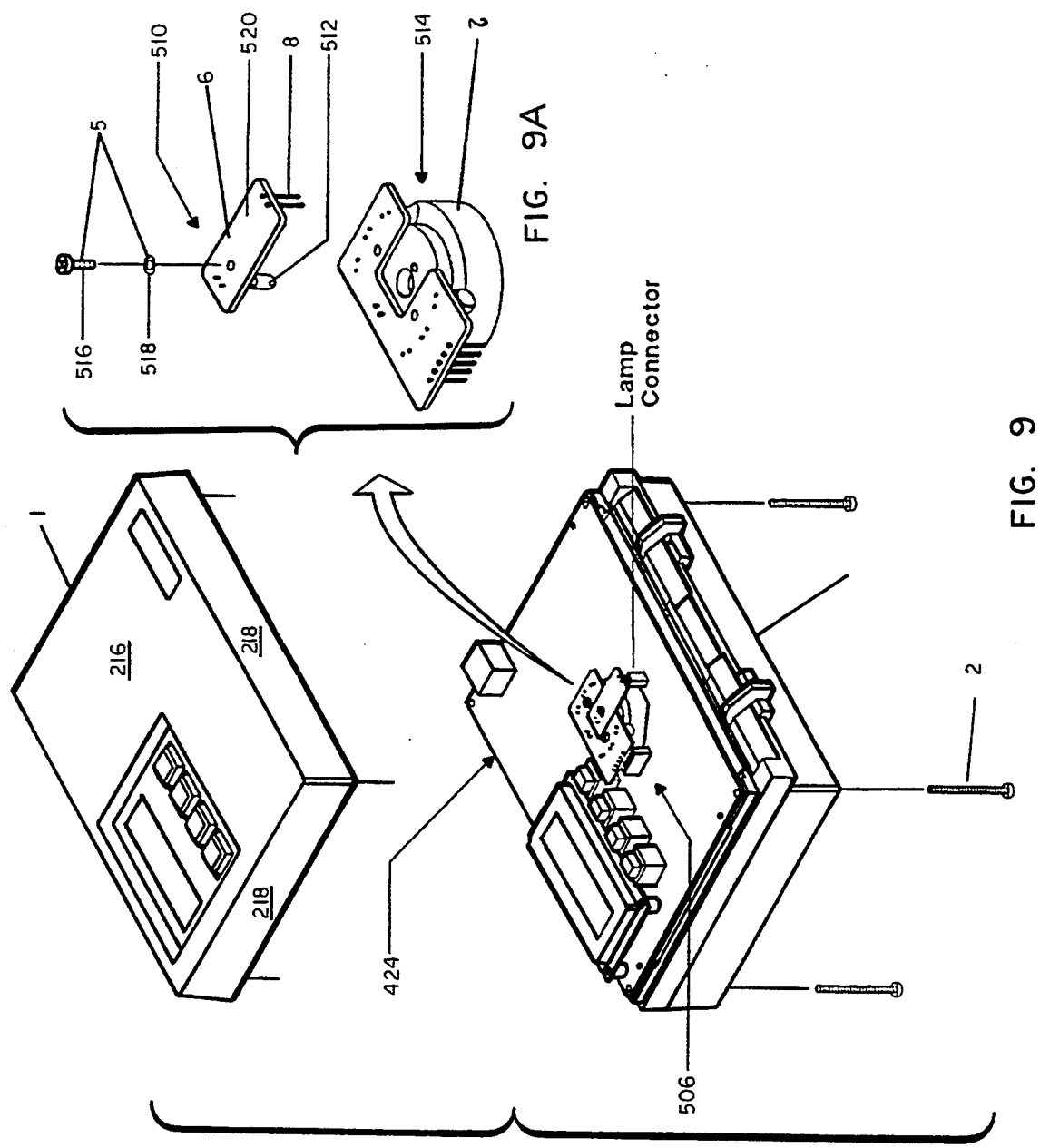
FIG. 9 is an exploded view of the apparatus shown in FIG. 5, and specifically showing elements of the lamp assembly of the apparatus.

Intermediate the top cover 212 and the bottom cover 214, and enclosed therebetween is a housing assembly 424 as primarily illustrated in FIGS. 7, 8 and 9, and specifically illustrated in an exploded view in FIG. 7. Referring specifically to FIG. 7, the housing assembly 424 comprises a motor assembly 426. The motor assembly 426 can be any of a series of conventional DC motors available on the commercial market. The housing assembly 426 further comprises a bottom housing 428 having a structural configuration as illustrated in FIG. 7. The bottom housing 428 includes an aperture 430 having slots 432 for purposes of receiving a drive wheel assembly 434 comprising an axle 436 with a series of drive wheels 438 axially positioned on the axle 436. The slots 432 are adapted to partially receive each of the drive wheels 438.

In addition to the drive wheel assembly 434, the housing assembly 424 also comprises an idler wheel assembly 440 comprising an elongated and cylindrical structure as further illustrated in FIG. 7. Attached to each end of the idler wheel assembly 440 are a pair of spindles 442. The housing assembly 424 further comprises a top housing 444 having a structural configuration as illustrated in FIG. 7. The top housing 444 includes an aperture 446 having an elongated configuration and through which the idler wheel assembly 440 is partially received. Located at each end of the elongated structure 446 is a brace 448 having recessed portions 450 adapted to rotatably receive the spindles 442 of the idler wheel assembly 440. Further, the braces 448 are spring loaded in a suitable manner so as to properly retain the idler wheel assembly 440.

Returning to the bottom housing 428 as illustrated in FIG. 7, the bottom housing further comprises a forward edge 452 having a slanted configuration and comprising a slightly recessed portion 454. The recessed portion 454 comprises a width appropriate for insertion of 35 mm film strips for color density measurements utilized in the apparatus 210. The bottom housing 428 additionally includes a slot 456 adapted to receive a conventional microswitch assembly 458. The microswitch assembly 458 can comprise a "read" switch which is enabled by movement of a control strip into the densitometer apparatus 210 so as to activate the motor assembly 426.

The bottom housing 428 also comprises a film guide bar 460 having an elongated configuration and further having nubs 462 or similar elements adapted to be secured into slots 464 located adjacent the forward edge 452 of the bottom housing 428. In addition to the foregoing elements, a pair of film guides 466 are also included with the housing assembly 424. Specifically, the film guides 466 comprise a "left" film guide 468 and a "right" film guide 470. The film guides provide a means for guiding the control strip into the densitometer apparatus 210. Although not specifically shown in FIG. 7, the forward edge 452 of the bottom housing 428 can also comprise a series of numbered indicia indicating the relative positioning of the film guides 466.

As further shown in FIG. 7, the motor assembly 426 can comprise a driven shaft 472 which is adapted to be received through one end of the axle 436 of the drive wheel assembly 434. Accordingly, when the motor assembly 426 is activated, the drive shaft 472 will cause the drive wheel assembly 436 to rotate.

The top housing 444 can further comprise an optics assembly holder 474 which includes an aperture 476 which provides a slot for purposes of obtaining the transmission and reflection density measurements. The assembly holder 474 further comprises an annular portion 476 having a series of upright standards 478 extending upwardly therefrom.

For purposes of interconnecting the top housing 444 with the bottom housing 428, a pair of standards 480 are located substantially diagonal from each other and on opposing ledges 482 extending along opposing edges of the bottom housing 428. Correspondingly, the top housing 444 includes a pair of slots 484 positioned so as to be aligned with the standards 480. The alignment between the standards 480 and the slots 484 is such that the top housing 44 is essentially "snap" fitted with the bottom housing 428.

Returning to FIGS. 5 through 9, the densitometer apparatus 210 further comprises a visual display device 490 which can comprise a conventional LCD display device. In addition, the apparatus 210 also includes a keyboard 492 having a series of four key switches 494, 496, 498 and 500. The key switches on the keyboard 492 are conventional switches for providing manual input entry for the densitometer apparatus 210.

As illustrated in FIG. 8, the actual visual display device 490 and keyboard 492 are positioned on an upper printed circuit board assembly 502. The upper board assembly 502 includes an aperture 504 through which an optics assembly 506 can be mounted and secured to the previously described optics assembly holder 474 located on the housing assembly 424. As further illustrated in FIG. 8, the upper board assembly 502 can be simply mounted to the housing assembly 424 by means of screws 508 or other suitable connecting means.

As illustrated in FIG. 9, the optics assembly 506 can comprise a lamp assembly 510 adapted to secure and hold a suitable and conventional light source lamp 512. The lamp assembly 510 is secured within a lamp housing 514 by means of a conventional screw 516 and washer assembly 518. The components comprising the lamp assembly 510 and lamp housing 514 are relatively conventional in design with respect to known densitometer apparatus. The lamp assembly 510 can include a lamp printed circuit board 520 on which appropriate circuitry associated with the light source lamp 512 can be located.

As further illustrated in FIG. 8, the densitometer apparatus 210 can comprise a lower optics assembly 522 which can be characterized as a lower board assembly. The lower board assembly 522 can comprise circuitry associated with transmission density measurements by the apparatus 210. As further shown in FIG. 8, the lower board assembly can comprise a series of pins 524 comprising conventional elements for interconnecting the circuitry of the PC board assembly 522 to other circuitry associated with the apparatus. In addition, the lower board assembly 522 can include a pin connector 526 specifically adapted for providing circuit connections with the motor assembly 426. In addition, the board assembly 522 can also comprise an additional pin connector 528 suitable for connecting the circuitry of the board assembly 522 to power from batteries or the like.

As still further shown in FIG. 8, the apparatus 210 can comprise a battery holder assembly 530 adapted to receive a series of rechargeable batteries 532. The batteries 532 can provide a means for operation of the apparatus 210 without requiring any type of utility or external power. However, it should be emphasized that such a battery arrangement is purely optional.

For purposes of providing installation and appropriate positioning of the battery holder assembly 530, the apparatus 510 can further comprise a battery pad 534 positioned below the lower set of the batteries 532. In addition, if desired, the apparatus 210 can also include a back label 535 and serial number label 536. In addition, located on top cover 212, and positioned to be received over the display 490 and keyboard 494 can be a nameplate 538. Finally, a label 540 or other suitable identification means can further be positioned on the top cover 212.

Returning again to FIG. 6, the top cover 212 further comprises, in one side surface 218, an aperture 542 with an electrical receptacle 544 located within but spaced slightly apart from the aperture 542. The receptacle 544 comprises an input/output (I/O) port for a conventional RS 232 interface for purposes of providing a means for inputting data to and outputting data from the densitometer apparatus 410.

Figure 6:
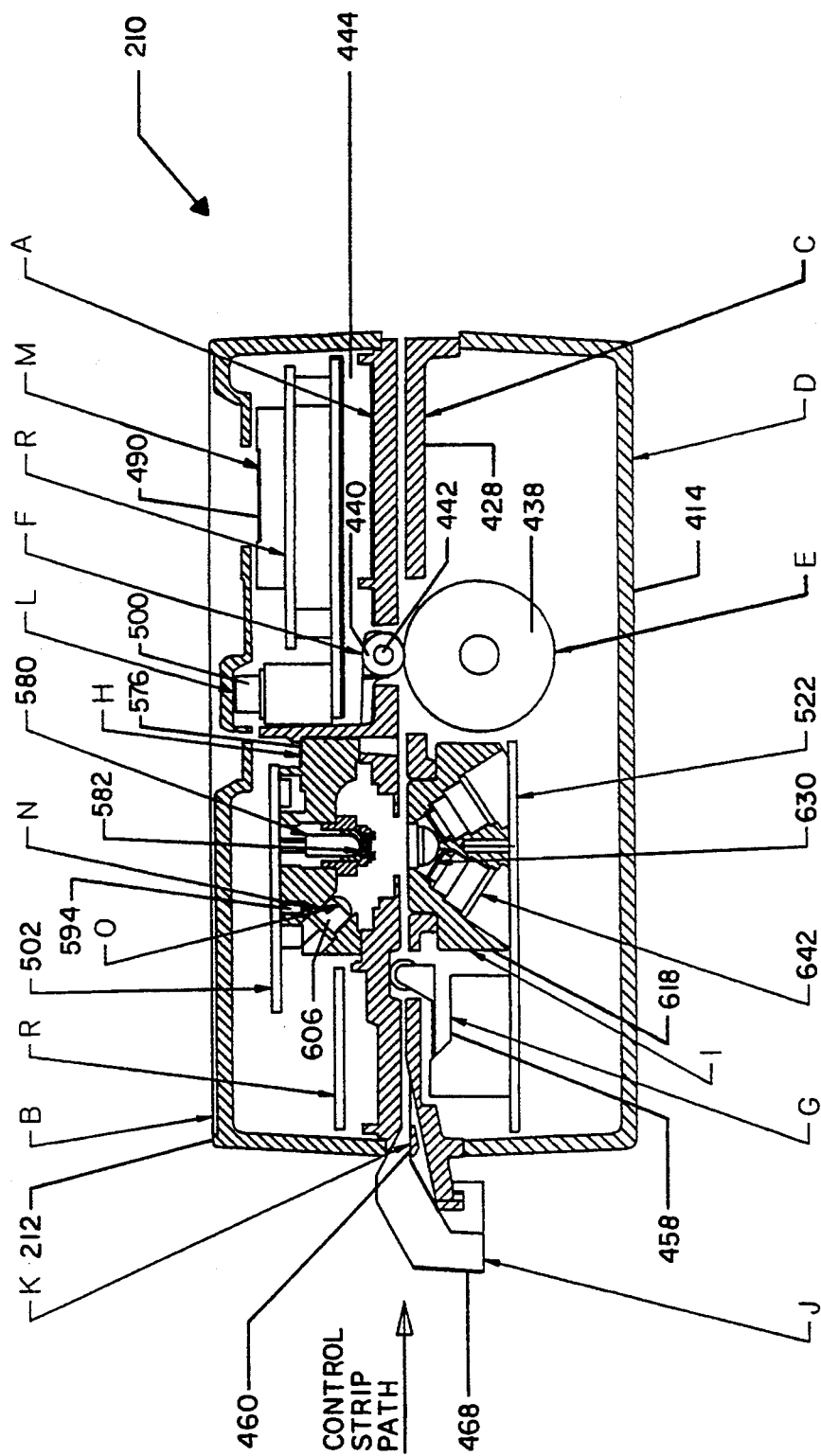
FIG. 6 is a cross-sectional diagram of a densitometer apparatus which may be utilized with the invention, illustrating the structural configuration of various elements of the apparatus.

In addition to the aperture 542, the densitometer apparatus 210 also comprises a second aperture 546 positioned on a side surface 222 of the bottom cover 214. Positioned within the aperture 546, but not specifically shown in FIG. 6, is an input receptacle for purposes of providing charger input for the batteries 532. Preferably, if the densitometer apparatus 410 comprises the batteries 532, the batteries 532 are conventional rechargeable batteries. The aperture 546, in combination with appropriate and conventional circuitry, can comprise a means for recharging the batteries 532 as necessary.

As further illustrated in FIG. 5, the recessed portion 454 of the housing assembly 424 can include a "diamond" or other appropriate indicia 548 for purposes of indicating the center of the path for color density measurements of the control strips. In addition, and as previously referenced, the forward edge 452 of the bottom housing 428 of the housing assembly 424 can include numerical indicia 550 centered with respect to the diamond indicia 548 and extending lengthwise across the forward edge 452. The numerical indicia 550 provide a means for indicating appropriate settings of the left and right film guides 468 and 470, respectively. As further shown in FIG. 5, the left and right film guides 468, 470 are conventional guides which are located at the forward edge 452 of the bottom housing 428 of housing 424. As shown in FIG. 7, the guides 468, 470 include elongated portions 552 which extend inwardly above the bottom housing 428 of housing assembly 424 and below the top housing 444. Each of the film guides 468, 470 is manually adjustable by the operator and comprise a means for guiding and controlling guidance of a control strip into the densitometer apparatus 410. FIG. 6 is a cross sectional view illustrating the configuration of the structural and circuit elements of densitometer apparatus 410 described herein.

Figure 10:
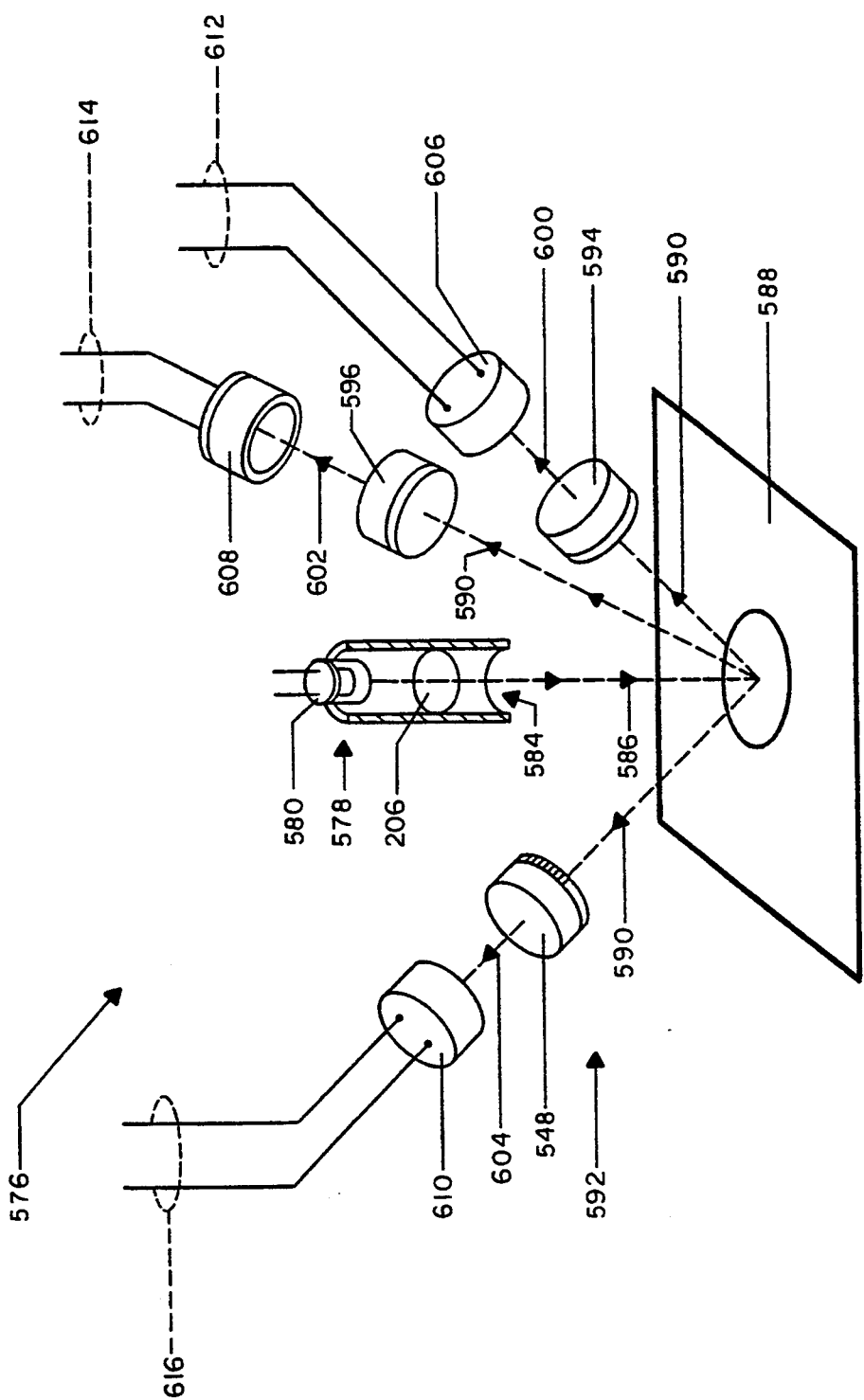
FIG. 10 is an illustration of the reflection optics assembly of the densitometer apparatus shown in FIG. 5.

Certain circuitry associated with the densitometer apparatus 210 will now be described with respect to FIGS. 10, 11 and 12. The densitometer apparatus 210 can include appropriate optics assemblies for measuring both transmission densities and reflection densities. FIG. 10 illustrates an exemplary reflection optics assembly 576 which can be utilized with the densitometer apparatus 210. Referring specifically to FIG. 10, and the numerical references therein, the densitometer apparatus 210 includes a light source unit or a lamp assembly 578 having a source light 580. Various standards have been developed for densitometer light source illuminants for optical density measurements in the field of photography. For example, densitometer standards have previously been described in terms of a tungsten lamp providing an influx from a lamp operating at a Planckian distribution of 3000K. Other suggested standards have been developed by ANSI and the International Organization for Standardization ("ISO"). These source light densitometry standards are typically defined in terms of the spectral energy distribution of the illuminant. The source light 580 preferably conforms to an appropriate standard and can, for example, comprise a filament bulb meeting a standard conventionally known in the industry as 2856K ANSI. As previously described, power for the source light 580 and other elements of the densitometer apparatus 410 can be provided by means of conventional rechargeable batteries or, alternatively, interconnection to AC utility power.

The source light 580 projects light through a collimating lens 582 which serves to focus the electromagnetic radiation from the source light 580 into a narrow collimated beam of light rays. Various types of conventional and well-known collimating lenses can be employed. The light rays transmitted through the collimating lens 582 project through an aperture 584. The dimensions of the aperture 584 will determine the size of the irradiated area of the control strip. Various standards have been defined for preferable sizes of the irradiated area. Ideally, the aperture 584 is of a size such that the irradiance is uniform over the entire irradiated area. However, in any physically realizable densitometer arrangement, such uniform irradiance cannot be achieved. Current standards suggest that the size of the irradiated area should be such that irradiance measured at any point within the area is at least 90% of the maximum value. In addition, however, aperture size is typically limited to the size of color bar areas to be measured, and is also sized so as to reduce stray light.

The light rays emerging from the aperture 584 (illustrated as rays 586 in FIG. 10) are projected onto the irradiated area surface of the control strip 588 under test. The control strip 588 may be a print balance strip or, alternatively, photographic paper or the like.

As the light rays 586 are projected onto the control strip 588, electromagnetic radiation shown as light rays 590 will be reflected from the control strip 588. As previously described in the section entitled "Background of the Invention", it is necessary to obtain quantitative measurements of this reflected light for purposes of determining the relative proportions of the light reflected from various object samples. As also previously described, it is substantially impossible to measure all of the light reflected from the control strip 588. Accordingly, standard detection configurations have been developed, whereby reflected light is detected at a specific angle relative to the illumination light rays 586 projected normal to the plane of the control strip 588. More specifically, standards have been developed for detection of reflected light rays at an angle of 45° to the normal direction of the light rays 586. This angle of 45° has become a standard for reflectance measurement and is considered desirable in that this configuration will tend to maximize the density range of the measurements. In addition, however, the 45° differential also represents somewhat of a relatively normal viewing configuration of a human observer (i.e. illumination at a 45° angle from the viewer's line of sight).

For purposes of providing light detection, a spectral filter apparatus 592 is provided. The filter apparatus 592 can include a series of filters 594, 596 and 598. The filters 594, 596 and 598 are employed for purposes of discriminating the cyan, magenta and yellow spectral responses, respectively. That is, each of the filters will tend to absorb light energy at frequencies outside of the bandwidth representative of the particular color hue of the filter. For example, the cyan filter 594 will tend to absorb all light rays, except for those within the spectral bandwidth corresponding to a red hue. By detecting reflected light rays only within a particular color hue bandwidth, and obtaining an optical density measurement with respect to the same, a "figure of merit" can be obtained with respect to the quality and color measurement of the control strip patch associated with that particular color hue.

Figure 1:
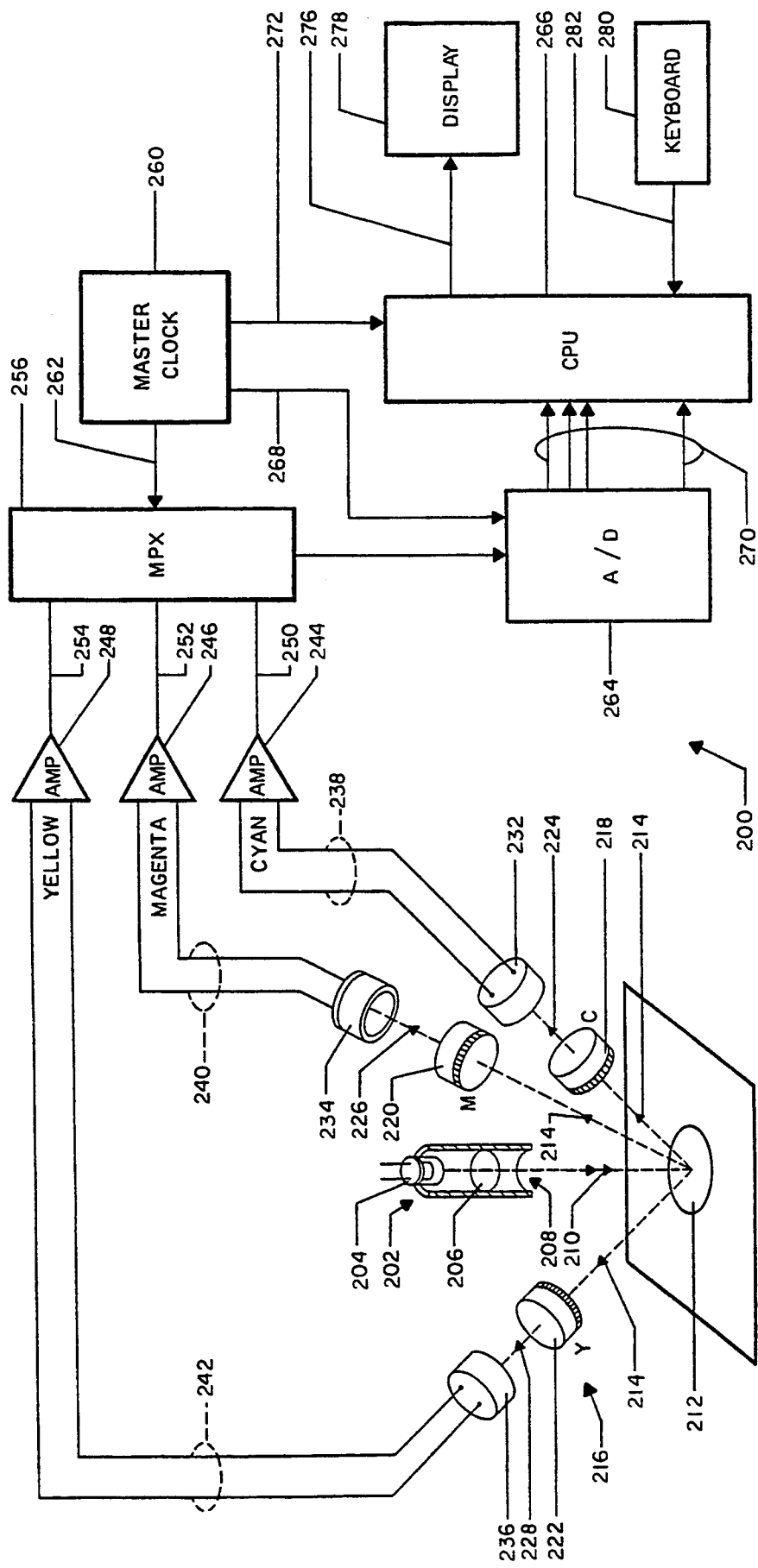
FIG. 1 is an illustrative embodiment of a prior art densitometer.
Figure 2:
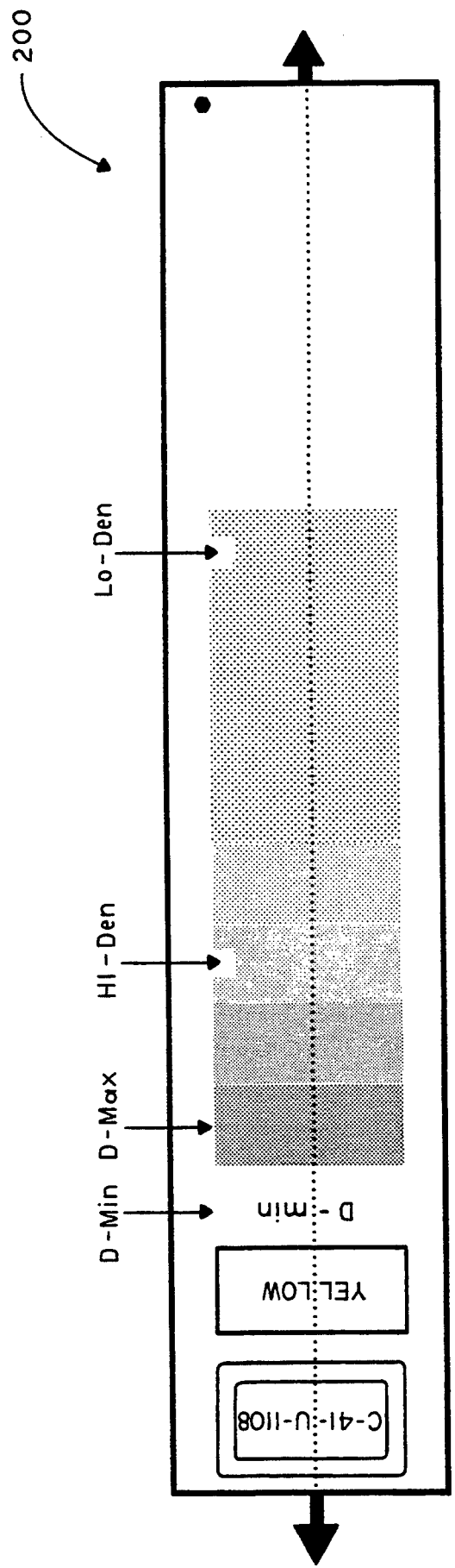
FIG. 2 is a prior art illustrative embodiment of a control strip which can be utilized with the densitometer illustrated in FIGS. 5-12.
Figure 3:
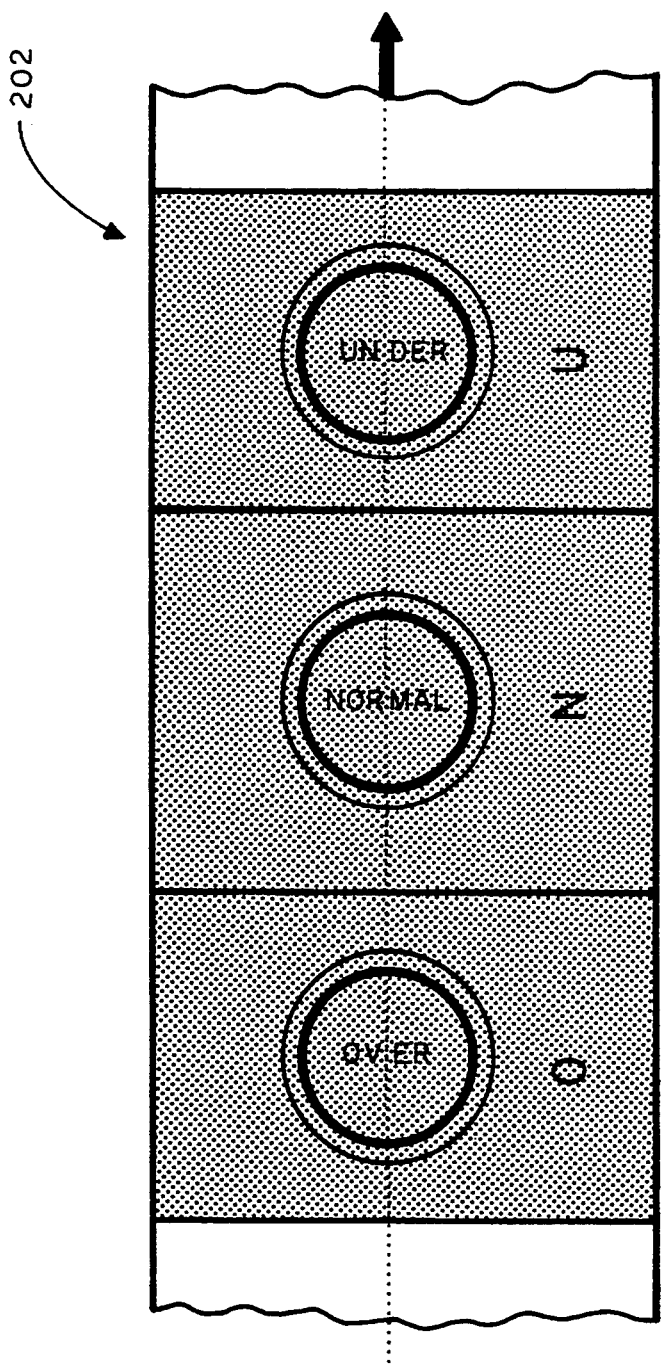
FIG. 3 is a prior art illustrative embodiment of a print balance control strip which can be utilized with the densitometer illustrated in FIGS. 5-12.
Figure 4:
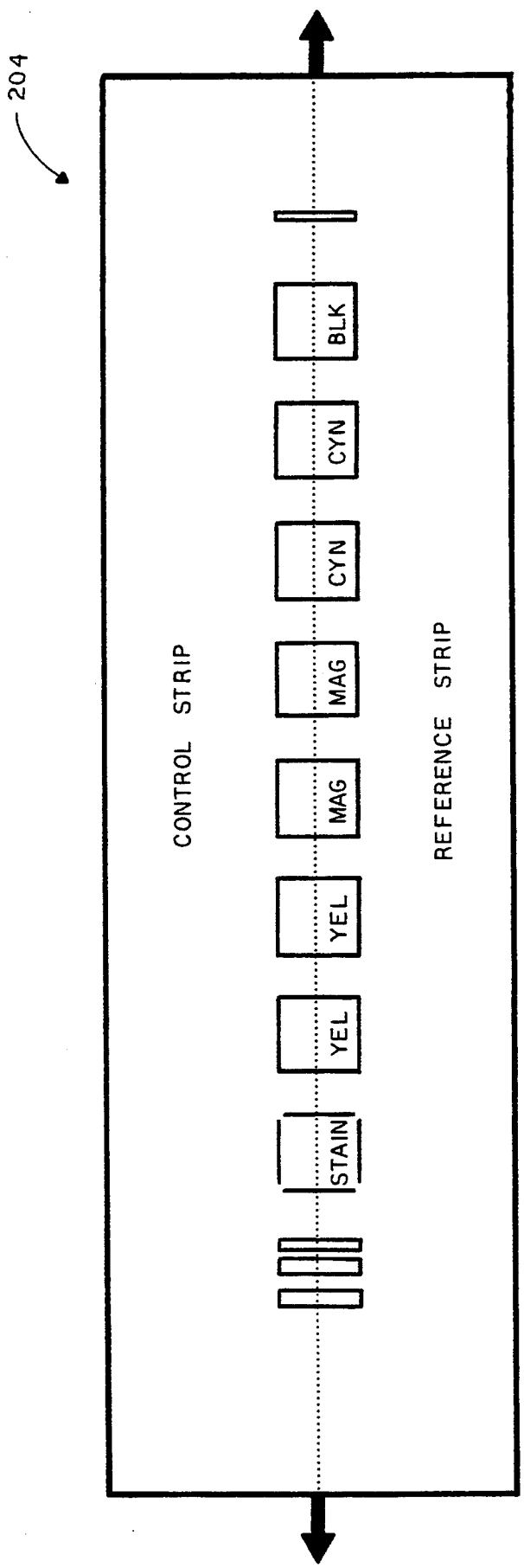
FIG. 4 is a prior art illustrative embodiment of a further control strip which can be utilized with the densitometer illustrate in FIGS. 5-12.

It is apparent from the foregoing that the actual quantitative measurement of color density for reflectance is dependent in substantial part on the spectral transmittance characteristics of the filters. Accordingly, various well known standards have been developed with respect to spectral characteristics of densitometer filters. Standards were previously described with respect to the prior art densitometer apparatus 100 illustrated in FIG. 1. For example, Status A filters can be employed.

Although the filters 594, 596 and 598 are illustrated in the embodiment shown in FIG. 10 as the cyan, magenta and yellow color shades, other color shades can clearly be employed. These particular shades are considered somewhat preferable in view of their relative permanence and because they comprise the preferred shades for use in reflection densitometer calibration. However, it is apparent that different shades of red, blue and green, as well as entirely different colors, can be utilized with the densitometer apparatus 210.

The spectral filters 594, 596 and 598 may not only comprise various shades of color, but can also be of any several specific types of spectral response filters. For example, the filters can comprise a series of conventional Wratten gelatin filters and infrared glass. However, various other types of filter arrangements can also be employed.

As further shown in FIG. 10, the portion of the reflected light rays 590 which pass through the filters 594, 596 and 598 (shown as light rays 600, 602 and 604, respectively) impinge on receptor surfaces of photovoltaic sensor cells. The sensor cells are illustrated in FIG. 10 as sensors 606, 608 and 610 associated with the spectral filters 600, 602 and 604, respectively. The sensors 606, 608 and 610 can comprise conventional photoelectric elements adapted to detect the light rays emanating through the corresponding spectral filters. The sensors are further adapted to generate electrical currents having magnitudes proportional to the intensities of the sensed light rays. As illustrated in FIG. 10, the electrical current generated by the cyan sensor 606 in response to the detection of light rays projecting through the filter 608 is generated on line pair 612. Correspondingly, the electrical current generated by the magenta sensor 608 is applied to the line pair 614, while the electrical current generated by the yellow sensor 610 is applied as output current on line pair 616. Photoelectric elements suitable for use as sensors 606, 608 and 610 are well known in the art, and various types of commercially available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral reflectance curve of the control strip sample 588 under test, and the spectral response curve of the corresponding filter. Accordingly, for a particular color shade represented by the spectral response curve of the filter, the magnitude of the electrical current represents a quantitative measurement of the proportion of reflectance of the control strip sample 588 within the frequency spectrum of the color shade.

Figure 11:
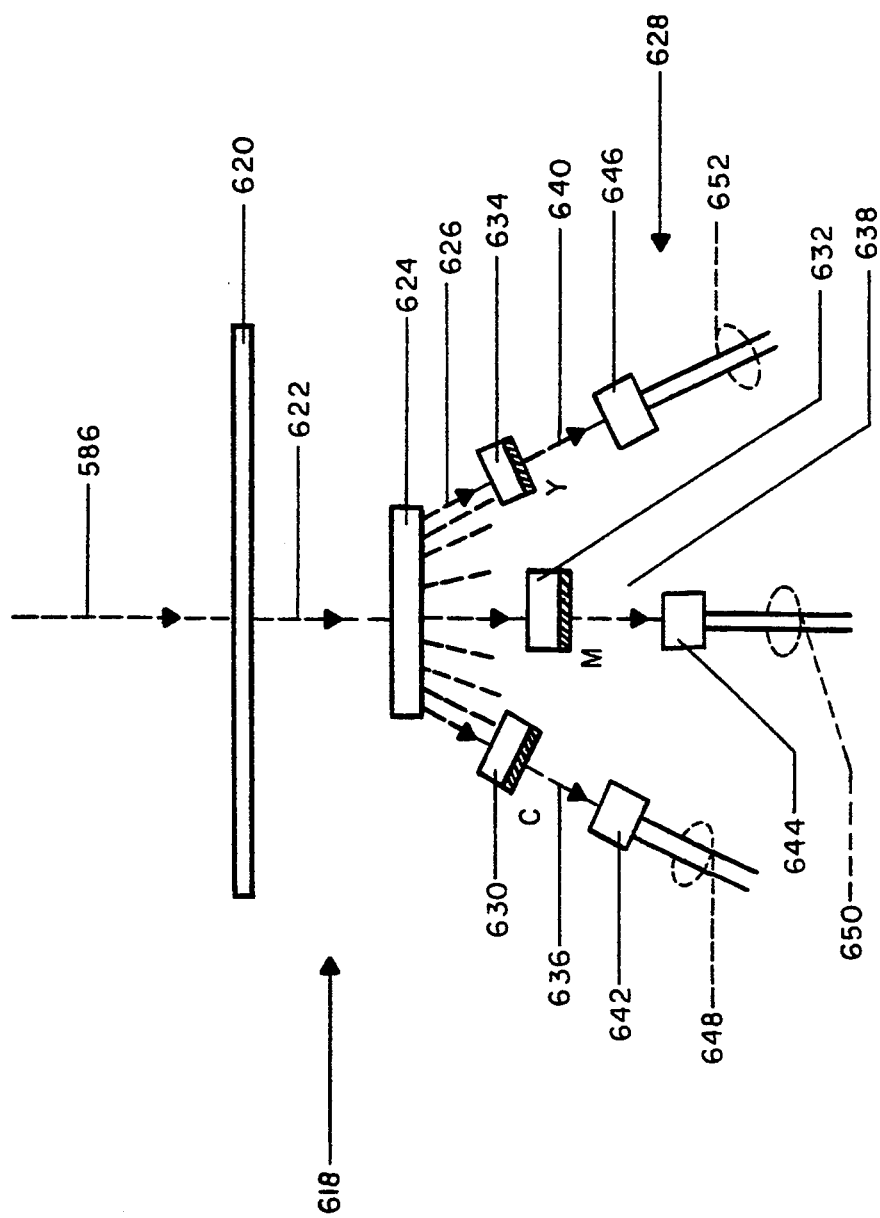
FIG. 11 is a partially schematic diagram of the transmission optics assembly of the densitometer apparatus shown in FIG. 5.

The densitometer apparatus 210 can include not only a reflection optics assembly 576 as previously described with respect to FIG. 10, but can further include a transmission optics assembly 618 depicted in simplified schematic form in FIG. 11. As previously described, the transmission optics assembly 618 is mounted on the lower board assembly 522. The exact method and structure associated with the mounting of the transmission optics assembly 618 will be apparent to one skilled in the art of optics and densitometer design, and will not be described in detail herein.

Referring specifically to FIG. 11, a film control strip 620 for which transmission density is to be measured is positioned so that the light rays 586 from the source light 580 (previously described with respect to FIG. 10) are projected from above the film control strip 620 onto the irradiated area surface of the strip 620. The film control strip 620 may be any of numerous types of materials for which the transmission density will provide an indication of the photographic quality of the associated photographic process. For example, the control strip 620 can be a film negative.

As the light rays 586 are projected onto the film control strip 620, electromagnetic radiation shown as light rays 622 will be transmitted through the control strip 620. For purposes of determining the relative proportions of the light transmitted through various object samples, it is necessary to obtain quantitative measurements of this transmitted light. However, it is substantially impossible to measure all of the light transmitted through the control strip 620. Accordingly, the transmitted light rays 622 are projected through a diffuser element 624 which causes the light rays to be substantially uniformly diffused. The diffuser element 624 is a relatively common and well known optical device, and can be characterized as an "opal." The diffused light rays transmitted through the diffuser element 624 are shown in FIG. 11 as light rays 626.

For purposes of providing light detection, a spectral filter apparatus 628 is provided. The filter apparatus 628, similar to the filter apparatus 592 described with respect to FIG. 12, comprises a series of three filters 630, 632 and 634. The filters 630, 632 and 634 are employed for purposes of discriminating the red, blue and green spectral responses (cyan, magenta and yellow), respectively. That is, each of the filters will tend to absorb light energy at frequencies outside of the bandwidth representative of the particular color hue of the filter. By detecting reflected light rays only within a particular color hue bandwidth, and obtaining an optical density measurement with respect to the same, a "figure of merit" can be obtained with respect to the quality of the object sample coloring associated with that particular color hue.

The spectral filters 630, 632 and 634 can be positioned at any of a number of desired angles relative to the plane of the opal 624 and the control strip 620. Although FIG. 11 shows the filters of the filter apparatus 628 in a two dimensional elevation view, the filters of the apparatus 628 will actually be angled in a manner similar to the configuration shown in the perspective view of FIG. 10 with respect to the reflection filters. Further, although the filters 630, 632 and 634 are illustrated in the embodiment shown in FIG. 11 as the red, blue and green color shades, other color shades can clearly be employed.

It is apparent from the foregoing that the actual quantitative measurement of color density of transmittance is dependent in substantial part on the spectral transmittance characteristics of the filters. Accordingly, various well-known standards have been developed with respect to spectral characteristics of transmittance densitometer filters. For example, these filters can be filters commonly characterized as Status M filters.

Like the reflection filters previously described, the filters of the filter apparatus 628 are maintained stationary and utilized to simultaneously receive the light rays 626 transmitted through the control strip 620. Accordingly, it is unnecessary for the user to manually rotate or otherwise sequentially move spectral transmittance filters into receptive positions.

As further shown in FIG. 11, the portion of the transmitted light rays 626 which pass through the filters 630, 632 and 634 (shown as light rays 636, 638 and 640, respectively) impinge on receptor surfaces of photovoltaic sensor cells. The sensor cells are illustrated in FIG. 11 as sensors 642, 644 and 646 associated with the spectral filters 630, 632 and 634, respectively. The sensors 642, 644 and 646 can comprise conventional photoelectric elements adapted to detect the light rays emanating through the corresponding spectral filters. The sensors are further adapted to generate electrical currents having magnitudes proportional to the intensities of the sensed light rays. As illustrated in FIG. 11, the electrical current generated by the red sensor 642 in response to the detection of light rays projecting through the filter 630 is generated on line pair 648. Correspondingly, the electrical current generated by the blue sensor 644 is applied to the line pair 650, while the electrical current generated by the green sensor 646 is applied as output current on line 652. Photoelectric elements suitable for use as sensors 642, 644 and 646 are well known in the art, and various types of commercially available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral transmittance curve of the control strip 620, and the spectral response curve of the corresponding filter. Accordingly, for a particular color shade represented by the spectral response curve of the filter, the magnitude of the electrical current represents a quantitative measurement of the proportion of transmittance of the control strip 620 within the frequency spectrum of the color shade.

Figure 12:
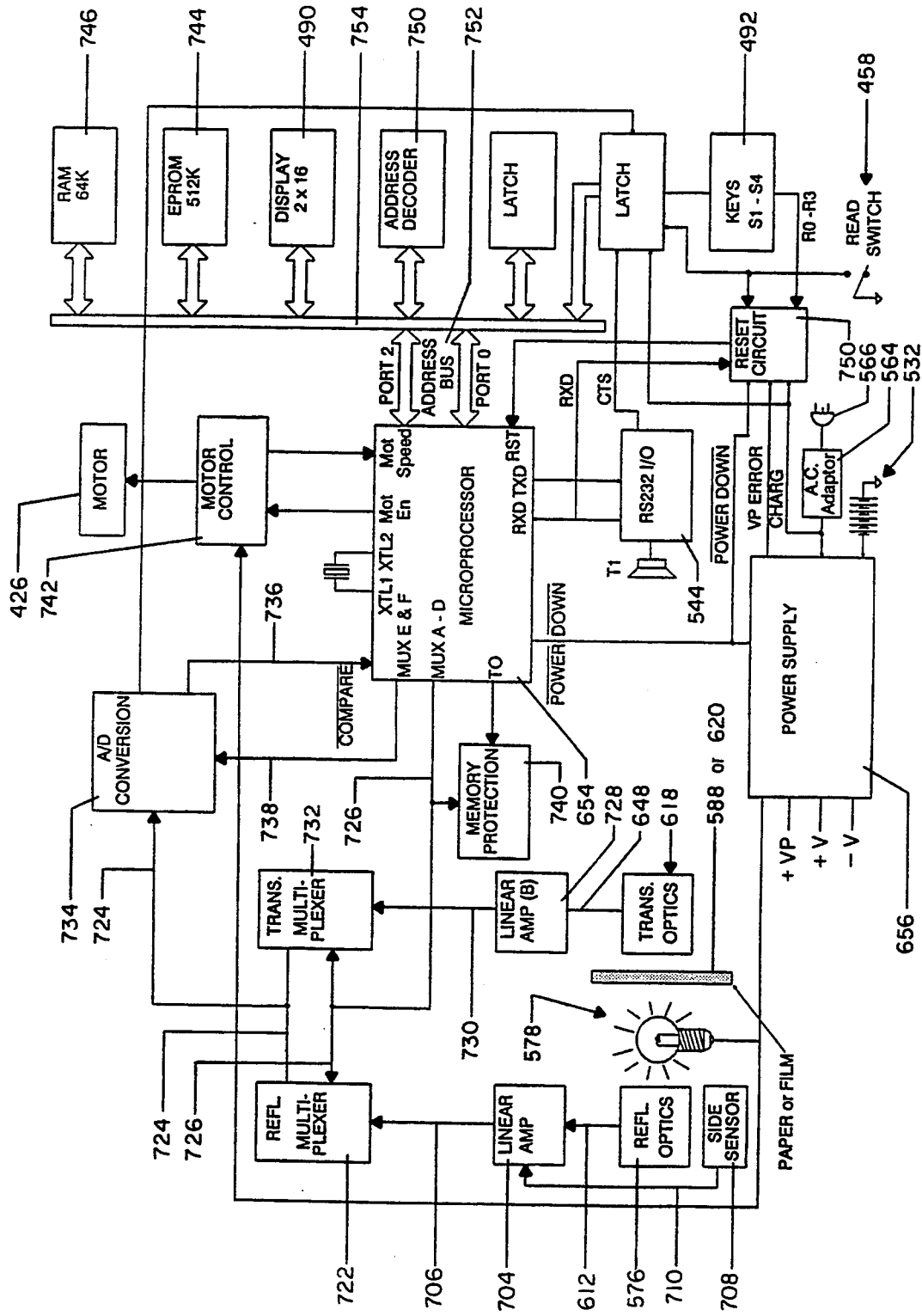
FIG. 12 is a partially schematic diagram of circuit elements of the densitometer apparatus shown in FIG. 5.

A general simplified block diagram of the electronics of the densitometer apparatus 210 is illustrated in FIG. 12. As shown therein, and as previously described, the densitometer apparatus 210 includes a light source unit 578 utilized for measuring color densities of the control strip 588 or 620. If the control strip is control strip 588, the apparatus 210 is adapted to measure reflection density. If the control strip is strip 620, the apparatus 210 is adapted to measure transmittance density through the use of the transmittance optics assembly 618. For purposes of description, although the reflection optics assembly 576 and the transmission optics assembly 618 each comprise three spectral filters and photosensors, and three paths for determining the color densities of different color hues of the spectrum, the electronics associated with the same will be described only with respect to one path. Accordingly, as shown in FIG. 12, only the line pair 612 is shown as being interconnected to the reflection optics assembly 576. Correspondingly, only the line pair 648 is shown as being interconnected with the transmission optics assembly 618. However, other line pairs as previously described with respect to FIGS. 10 and 11 will be interconnected to each of the optics assemblies 576 and 618.

As further shown in FIG. 12, the densitometer apparatus 210 includes a conventional microprocessor 654 utilized for purposes of obtaining data representative of color densities of a control strip under test, and further utilized to control various activities associated with operation of the apparatus 210. For these purposes, the microprocessor 654 will comprise various control programs adapted to perform a number of functions associated with operation of the apparatus 210. The relevant control programs will become apparent from the functions and the general operation of the densitometer apparatus 210 as described in subsequent paragraphs herein. Accordingly, the actual control programs will not be described in detail.

Returning to FIG. 12, the densitometer apparatus 210 includes a relatively conventional power supply 656. The power supply 656 is adapted to provide power to various elements of the circuitry of apparatus 410.

When the reflection optics assembly 576 is utilized, an electrical current representative of the reflectance is applied on line pair 612 as an input signal to the conventional linear amplifier 704. The amplifier 704 is responsive to the current output of the associated sensor on line pair 612 to provide a means for converting low level output current from the respective sensor on the corresponding line pair 612 to a voltage level signal on the conductor 706. The voltage level of the signal on the conductor 706 is of a magnitude suitable for subsequent analog-to-digital (A/D) conversion functions. Such amplifiers are well known in the circuit design art and are commercially available with an appropriate volts per ampere conversion ratio, bandwidth and output voltage range. The magnitude of the output voltage on conductor 706 represents the intensity of reflected light rays transmitted through the corresponding spectral filter.

The densitometer apparatus 210 also includes a side sensor 708 which is utilized to compensate for changes in lamp intensity of the source light 578. Output from the side sensor 708 is applied to the linear amplifier circuit 704 on transmission line 710.

Each of the voltage signal outputs from the linear amplifier circuitry for each color channel are applied as input signals to a single conventional multiplexer 722. For example, the output voltage from linear amplifier circuitry 704 is applied on the transmission line 706 as an input signal to the reflection multiplexer 722. It should be emphasized that although there are three linear amplifier circuits, one for each color channel, only a single reflection multiplexer 722 is provided. The multiplexer 722 operates so as to time multiplex the output signals from each of the linear amplifier circuits (including linear amplifier circuit 704) onto the conductive paths 724 and 726. Timing for operation of the reflection multiplexer 722 can be provided by means of clock signals from a conventional master clock. During an actual density measurement of a control strip, the densitometer apparatus 210 will utilize a segment of the resultant multiplexed signal which sequentially represents a voltage output signal from each of the linear amplifier circuits associated with different color channels.

Correspondingly, as further illustrated in FIG. 12, the current output signal on line pair 648 from the transmission optics assembly 618 is applied to a linear amplifier circuit 728. A linear amplifier circuit 728 is provided for each of the color channels associated with the transmission optics assembly 618. The linear amplifier circuit 728 provides a means for converting low level output current from the respective sensor on the corresponding line pair 648 to a voltage level signal on the conductor 730. The voltage level of the signal on the conductor 730 is of a magnitude suitable for subsequent A/D conversion functions.

As further shown in FIG. 12, the voltage signal output from the linear amplifier circuitry 728 on conductive path 730 is applied as an input signal to a conventional transmission multiplexer 732. Like the reflection multiplexer 722, the transmission multiplexer 732 operates so as to time multiplex the output signals from each of the linear amplifier circuits associated with the transmission optics assembly 618. Again, timing for operation of the multiplexer 732 can be provided by means of clock signals from a master clock. During an actual transmission density measurement of a control strip, the densitometer apparatus 410 will utilize a segment of the resultant multiplexed signal which sequentially represents a voltage output signal from each of the linear amplifier circuits associated with the transmission optics assembly 618.

The resultant multiplexed signal from the transmission multiplexer 732 is applied as an output signal on the conductive path 724. The resultant multiplexed signal from either the reflection multiplexer 722 or the transmission multiplexer 732 is applied as an input signal to a conventional A/D converter 734. The A/D converter 734 comprises a means for converting the analog multiplexed signal on the conductive path 724 to a digital signal for purposes of subsequent processing by the microprocessor 654. The A/D converter 734 is preferably controlled by means of clock pulses applied from a conventional master clock.

As illustrated in FIG. 12, the digital output signals from the A/D converter 734 are applied as input signals on transmission line 736 to the microprocessor 654. Further, the microprocessor 654 is utilized to provide various control signals to the reflection multiplexer 722 and transmission multiplexer 732 (on transmission line 726). Still further, control signals are also applied from the microprocessor 654 to the A/D converter 734 by means of the transmission line 738. In addition to the foregoing elements, the densitometer apparatus 210 also comprises a memory protection circuit 740 which is further controlled in part by the microprocessor 654. The memory protection circuit 740 is conventional in design and comprises a well known arrangement for protecting the memory against power surges and power outages.

As previously described, the densitometer apparatus 210 also comprises a motor 426. The motor is operated under control of a motor control circuit 742 as illustrated in FIG. 12. Correspondingly, the motor control circuit 742 is controlled by the microprocessor 654, with power being supplied by the power supply 656. Various types of motor control circuits can be employed with the densitometer apparatus 210.

The microprocessor 654 is utilized for control of various functions associated with the densitometer apparatus 410. Numerous types of conventional and commercially available microprocessors can be employed for the microprocessor unit 654. An exemplary microprocessor could, for example, comprise the Intel 80C31 8-Bit CMOS Microcomputer commercially available from the Intel Corporation.

The densitometer apparatus 210 also comprises an address decoder 750 interconnected to the address bus 752 of the microprocessor 654. The address decoder 750 is utilized to decode the address range for the various devices associated with the bus 754. The address decoder 750 is conventional in design.

As also previously described, the densitometer apparatus 210 includes an EPROM 744 which can comprise, for example, a CMOS 512K EPROM. In addition, the apparatus 410 can also comprise the random access memory 746. The RAM 746 can, for example, comprise an 8192 byte static random access memory.

As also previously described, the densitometer apparatus 210 can include a series of key switches 492. These key switches will operate in conjunction with a reset circuit 750 as illustrated in FIG. 12. As previously described, the reset circuit 750 is controlled in part by the microprocessor 654.

Greater detail with respect to the previously described elements of the densitometer apparatus 210, and the operation thereof with respect to uses of control strips are described in the previously referenced Cargill et al application. Briefly, when a particular control strip is to be "selected" by the operator, the microprocessor 654 is programmed so as to generate appropriate data to the display 490 which will identify various aspects of the control strip. In addition, the apparatus 210 can display various information on the display 490 relating to the guide setting positions for the guides 468 and 470.

The densitometer apparatus 210, in summary, is adapted to operate as an automated instrument for measuring color densities of film control strips, paper control strips and printer balance strips. The apparatus 210 is motorized and comprises fixed optics assemblies for purposes of measuring the color densities. As desired, the microprocessor 654 can be programmed so as to appropriately sort data for measuring various control strip fields. The adjustable guides accommodate differing sized control strips for use with the apparatus 210.

Figure 13:
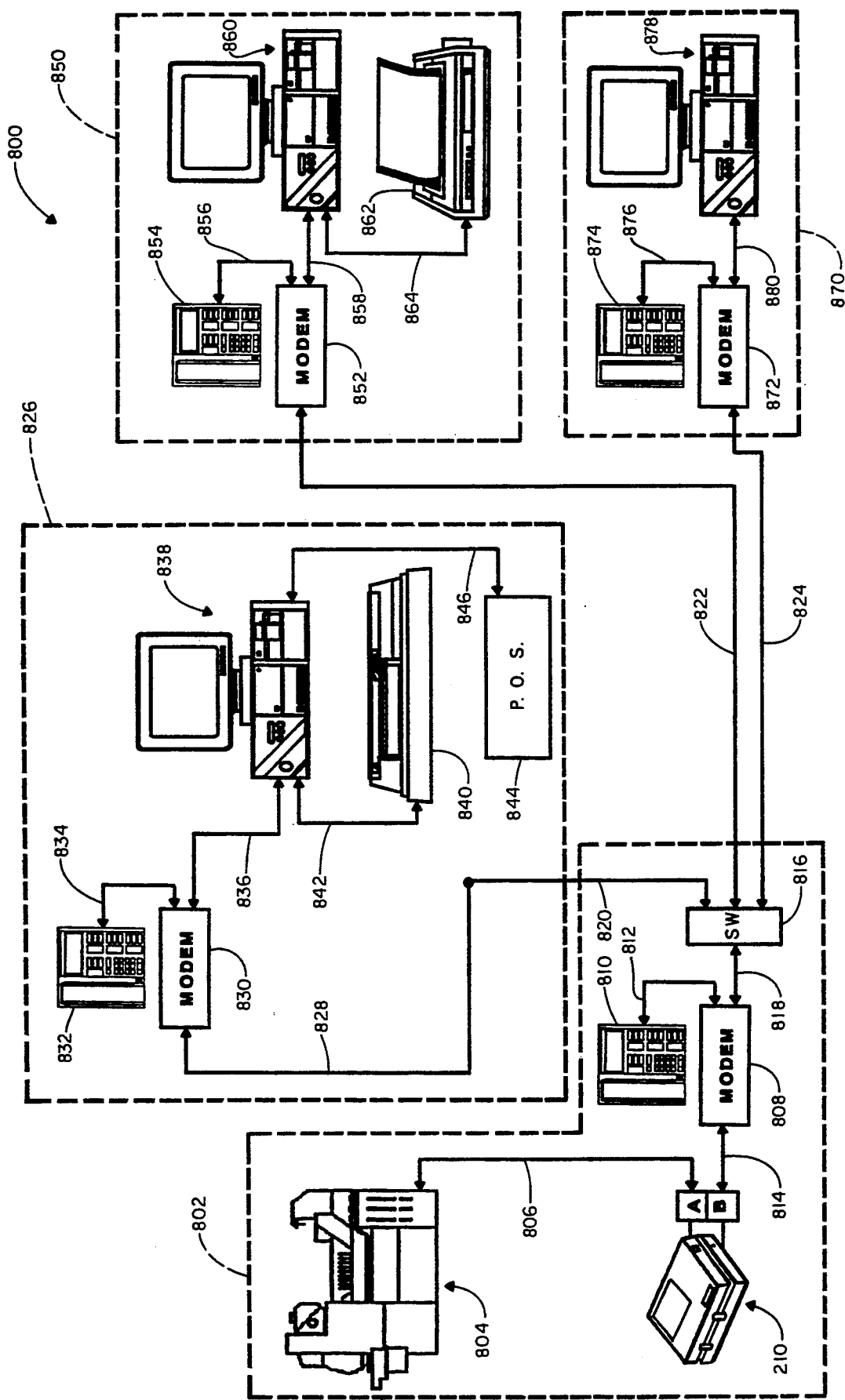
FIG. 13 illustrates a network configuration which can be adapted for use with the network message log structure.

In accordance with aspects of the invention as described in subsequent paragraphs herein, the densitometer 210 can be employed in a film or paper processing network configuration 800 as illustrated in block diagram form in FIG. 13. The network configuration 800 can include a series of processing laboratories 802, only one of which is illustrated in FIG. 13. Each processing laboratory 802 can be one of a series of physically separated laboratories for purposes of providing processing functions requiring color measurement procedures. For example, as shown in FIG. 13, the processing laboratory 802 can include a conventional film or paper processing apparatus 804 utilized for purposes of preparation of color film or paper employing electrophotographic or various printing techniques requiring color technology. Apparatus such as the film or paper processing apparatus 804 are well known in the art and are manufactured and sold by various domestic and foreign companies, including the Eastman Kodak Company.

The film or paper processing apparatus 804 is interconnected through one or more communication lines 806 to a densitometer 210. The actual interconnection to the densitometer 210 is achieved through the interface 544 previously described with respect to FIG. 12, and through port A of the interface 544. With the interconnection of film or paper processing apparatus 804 to the densitometer 210 through communication lines 806, data signals can be transmitted between the densitometer 210 and apparatus 804. In this regard, the apparatus 804 can include a conventional computer processing system (not shown) for purposes of sending to and receiving signals from the densitometer 210 through port A of the interface 544. The interface 544 can be a serial interface with port A being a bidirectional port allowing bidirectional serial communication between the apparatus 804 and densitometer 210. Concepts and structure associated with providing intercommunication between a physically separate computer processing system (such as one which may be employed with the apparatus 804) and a densitometer such as a densitometer 210 are described in the previously reference Peterson et al patent.

The processing laboratory 802 can also include a conventional modem 808 interconnected with a conventional telephone apparatus 810 through signal lines 812. Modems which can be utilized in accordance with the invention as modem 808 are well known in the prior art. For example, the modem 808 can comprise a Hayes or Hayes-compatible modem. The modem 808 is interconnected in a bidirectional format with port B of the interface 544 through a conventional communication line 814. Signals in the form of informational data can be transmitted from a location external to the processing laboratory 802 through the modem 808, communication line 814 and port B of the interface 544 to memory locations in the densitometer 210. Correspondingly, signals representative of various data can be transmitted from densitometer 210 through port B of interface 544, bidirectional communication line 814 and modem 808 to externally located devices.

In this regard, the modem 808 and telephone set 810 can be utilized so as to selectively acquire data from or transmit data to various locations dependent upon a particular telephone line or number utilized for transmission. To provide for such selective transmission, the modem 808 can be configured so as to have two or more separate telephone number lines being received within the processing laboratory 802. For purposes of functionally illustrating this arrangement, FIG. 13 illustrates a symbolic switch 816 connected to the modem 808 through a bidirectional communication line 818. The switch 816 is interconnected with three telecommunication lines identified as lines 820, 822 and 824. Again, the switch 816 is symbolic in nature and represents the concept of utilizing, for example, three separate telephone number lines with the modem 808 and telephone set 810.

The bidirectional telecommunications line 820 represents a conventional telecommunications line which can be switched through local or national telephone networks and can be interconnected to a system such as the retail system 826 also illustrated in FIG. 13. The retail system 826 can include a communication line 828 interconnected with a conventional modem 830 and telephone set 832. The telephone set 832 is interconnected in a conventional manner to the modem 830, through a communication line 834. Correspondingly, the modem 830 can be connected through a conventional bidirectional communication line 836 to a computer processing system symbolically represented as processing system 838 in FIG. 13. The computer processing system 838 can include a processor configuration with an interconnection to a peripheral device such as a printer 840 interconnected to the processor through communication lines 842. Correspondingly, other peripheral devices, such as a conventional retail "point of sale" system represented as point of sale device 844 can be interconnected to the processor 838 through communication lines 846. The retail system 826 represents a system such as that which may exist in a retail store of a film processing company. The capability of interconnecting the retail system 826 to the processing laboratory 802 provides for bidirectional transmission of data relating to various film developing activities, such as status of film processing and the like.

In addition to the retail system 826, FIG. 13 also illustrates a host system 850 which can be interconnected to the processing laboratory 802 through the telecommunications line 822. The host system 850 also includes a conventional modem 852 with a telephone set 854 interconnected thereto by communication line 856. Correspondingly, the modem 852 is interconnected through a bidirectional communication line 858 to a host processing system 860 symbolically illustrated in FIG. 13. The host processing system 860 can comprise a conventional computer processor having interconnections to peripheral devices such as the printer device 862, with transmission of data signals to the printer device 862 from the host processor 860 through communication line 864. As will be described in subsequent paragraphs herein, the host system 850 can provide a remotely located system for purposes of controlling functions associated with the processing laboratory 802, and also for receiving data from processing laboratory 802 related to the film or paper processing activities.

As another example of an interconnection with the processing laboratory 802, FIG. 13 illustrates a quality assurance system 870 interconnected to the processing laboratory 802 through telecommunications line 824. Specifically, the quality assurance system 870 includes a conventional modem 872 having a control connection to a conventional telephone set 874 through communication line 876. The quality assurance system 870 also includes a quality control processor 878 having a communications interconnection to the modem 872 through bidirectional communication lines 880.

The network configuration illustrated in FIG. 13 shows an exemplary network which may be utilized for control and other activities associated with a film or paper processing company. More specifically, with respect to the processing laboratory 802, data associated with film processing procedures related to the film or paper processing apparatus 804 can be transmitted to the densitometer 210 through communications line 806 and port A of the interface 544.

With data supplied to the densitometer 210 from the film or paper processing apparatus 804, the densitometer 210 can communicate such data, along with other information, to any of the systems 826, 850 or 870 of the network configuration 800. For example, the retail system 826 can be physically located at a retail store of the film processing company or similar organization, and information regarding the status of film processing procedures or the like can be communicated to the system 826 through the communications apparatus previously described herein. Correspondingly, the quality assurance system 870 can be utilized to receive data from the processing laboratory 802 regarding the quality of color processing and similar functions associated with the film or paper processing functions of the apparatus 804. An example of such an arrangement is known in the industry as the Kodak Colorwatch System. With this type of a system, signals can be transmitted from the quality assurance system 870 to the densitometer 210 of the processing laboratory 802, so as to essentially command the densitometer 210 to transmit informational data regarding color quality of the film processing apparatus 804 to the quality assurance system 870. As previously described with respect to FIG. 12, data transmitted to the densitometer 210 through port A or port B is applied through the interface 544 and into the memories 744, 746 of the densitometer 210 via the address bus 752. Correspondingly, data transmitted from the memories 744, 746 of densitometer 210 are also applied through the interface 544 to port A or port B as selected in accordance with software operating under control of the processor 654 of the densitometer 210.

Various communications can also be established between the processing laboratory 802 and the host system 850. The host system 850 can essentially be adapted to control and manage each of a plurality of processing laboratories 802, although FIG. 13 illustrates only one of the processing laboratories 802. More specifically, the processor system 860 of the host system 850 can include appropriate computer software for collecting and displaying color measurement and related data from each of the processing laboratories 802, and can also be adapted to essentially create and manage data transmitted to the processing laboratories 802.

The following paragraphs generally describe concepts associated with communications between the processing laboratory 802 and the host system 850. In particular, the following description is primarily directed to specific communication procedures and options related to communications between the densitometer 210 of the processing laboratory 802 and the processor 860 of the host system 850. Concepts associated with communications employing a conventional telecommunications line such as telecommunications line 822 and conventional modems 808, 852 and telephone sets 810, 854 are well known in the art and will not be described in any detail herein. Further, basic principles associated with communications between an external computer system and a densitometer employing a standard serial interface are described in detail in the afore-referenced Peterson et al, U.S. Pat. No. 4,591,978 issued May 27, 1986. Still further, concepts associated with the use of a processor, memories, display, keys and a serial interface within a densitometer such as the densitometer 210 of processing laboratory 802 are described in several references, including the afore-referenced Cargill et al patent application and the commonly assigned and currently pending U.S. Patent application Ser. No. 07/679,995 filed Mar. 29, 1991. Accordingly, in the following description, details associated with the receiving and transmitting of data among internal elements of the densitometer 210, along with details associated with the operation of an internal processor such as the microprocessor 654 shown in FIG. 12, will not be described in detail herein.

As earlier described, it is advantageous for the host system 850 to have the capability of controlling or, at least, monitoring activities undertaken by each of the processing laboratories 802. For such functional operation, the densitometer 210 of each of the processing laboratories 802 can include various hardware structure and software to provide interactive communications between the processing laboratory 802 and the host system 850. Correspondingly, communications hardware and software can also be resident at the host system 850 for purposes of performing such functions. In addition to the modem 852 and the conventional telephone set 854, the host system 850 can include, as the processor 860, a relatively conventional processor such as an IBM-compatible personal computer, with appropriate memory. Such computer systems are well known in the art and details associated with the same will not be described herein. Details associated with a specific processor configuration and the operation thereof with associated memories and with input/output interfaces are described in the commonly assigned and currently pending U.S. Patent application Ser. No. 07/534,205 filed on Jun. 7, 1990 and entitled Densitometer with Error Correction.

For purposes of providing interactive communications between the host system 850 and the processing laboratory 802, the host system 850 can include appropriate communications software having particular functions adapted for use with densitometers, such as the densitometer 210, and relating to color measurement and analysis procedures associated with the film or paper processing apparatus 804. For purposes of providing a "user friendly" system for the operator at the host system 850, the host system 850 can include appropriate software within the processing apparatus 860 for purposes of allowing the user to select particular functions to be performed relating to each of the processing laboratories 802.

Figure 14:
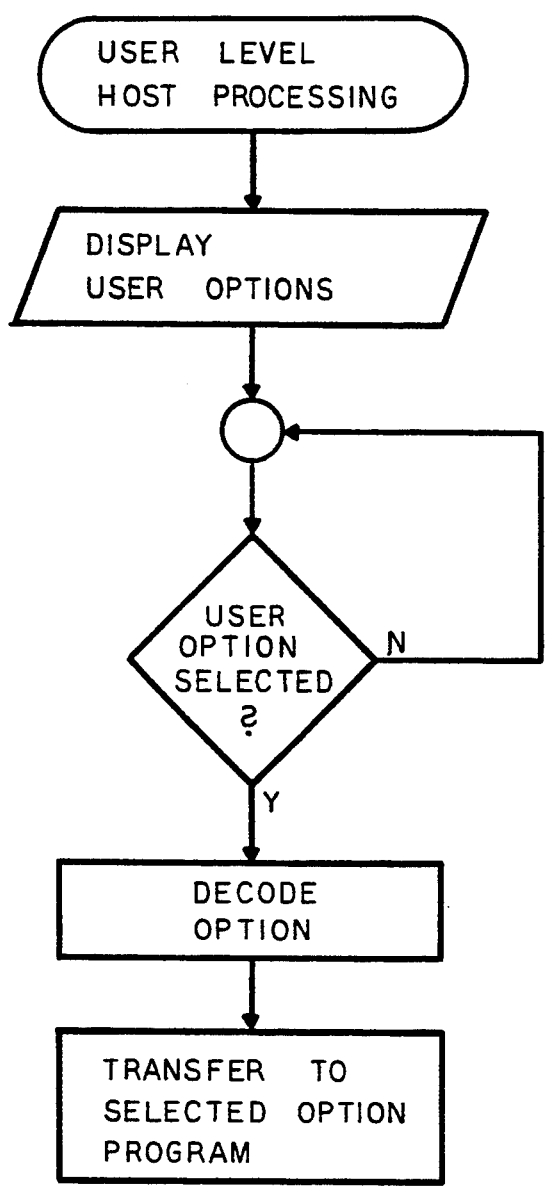
FIG. 14 illustrates an exemplary functional sequence diagram for use by an operator at the host system for performing various communications functions.

At the user level, the host processor 860 can include on its visual display a "menu" of particular functions which may be performed by the user operator. FIG. 14 illustrates a sequence diagram for the software resident in the host processor 860 for purposes of providing interactive communications with the operator. With reference to FIG. 14, the software resident within the host processor 860 can generate an appropriate display of "user options" for purposes of allowing the user to select particular functions to be performed with respect to intercommunications with the densitometer 210 of each of the processing laboratories 802. As further shown with respect to FIG. 14, the display of the user options can be continuously generated by the host processor 860 until a particular user option is selected by the operator. Such an option selection can be performed by means of the user operator transmitting the desired option to the host processor by means of input of data through a keyboard or similar input apparatus. When the host processor 860 has detected an operator input, the particular key data entered by the operator can be decoded, by conventional means, so as to determine the particular option selected by the user operator. When the option has been appropriately decoded, control can be transferred by the host processor to the particular program or functional software sequence adapted for performance of that particular functional option.

For example, data relating to color measurements periodically undertaken by the densitometer 210 with respect to film or paper produced by the film or paper processing apparatus 804 may be periodically stored within the random access memory 746 of the densitometer 210. Further, as described in detail in the aforereferenced Cargill et al patent application, color measurement and analysis data associated with control and reference color strips may also be stored in appropriate memories of the densitometer 210. The user operator may wish to obtain a display or appropriate printout of this color measurement data. Accordingly, the options available to the user at the host processor 860 should include an option to obtain data from the densitometer 210. Such an option can also include further "suboptions" associated with obtaining such data. For example, it would be possible for this user option to include the capability of obtaining color measurement data stored within the densitometer 210 only subsequent to a particular date and time. Further, as earlier described, it would also be possible to include a sub-option which provides for such data to be generated on a visual display screen of the host processor 860 or, alternatively, to be further transmitted to a peripheral device such as the printer 862 through appropriate communications line 864.

As another potential option associated with intercommunications between the processing laboratory 802 and the host system 850, it is also possible for the user to be given the option to transmit appropriate data from the host processor 860 to the densitometer 210, for purposes of storing such data within the memory 746 of the densitometer 210 or, alternatively, to have such data displayed on the display 490 of the densitometer 210. Still further, and as described in subsequent paragraphs herein in greater detail, the film or paper processing apparatus 804 may include elements which are adapted to directly receive data from the host system 850, without a requirement of data storage or analysis by the densitometer 210. For this purpose, and again as described in subsequent paragraphs herein, the processing laboratory 802 can have a "pass through" option associated with the densitometer 210 and its associated ports A and B, such that data is essentially directly transmitted between the processor 860 and the film or paper processing apparatus 804 through ports A and B of the interface 544 of densitometer 210. Other potential options associated with functions which can be performed relating to communications between the processing laboratory 802 and the host system 850 are also described in subsequent paragraphs.

Figure 15:
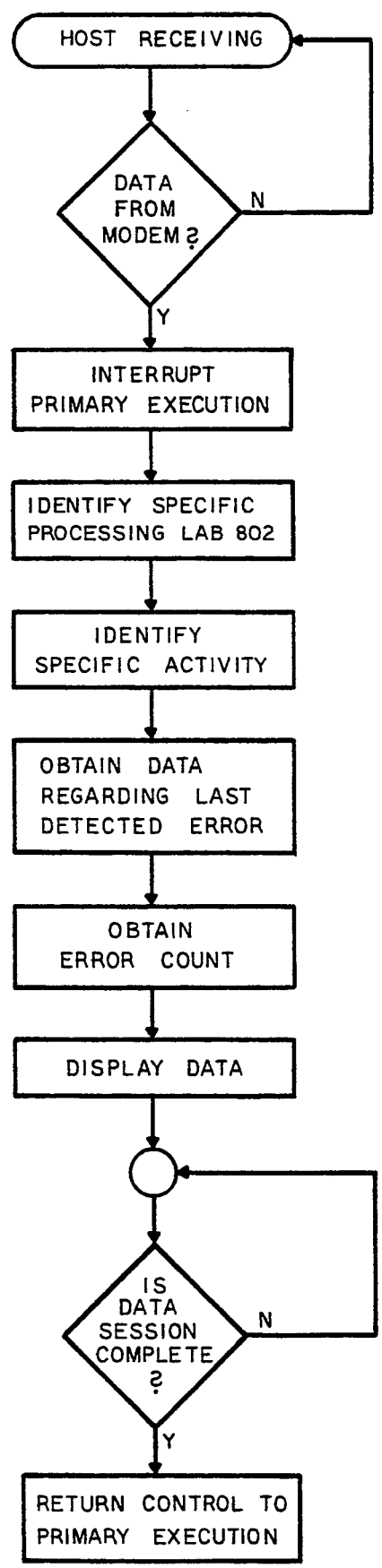
FIG. 15 is a functional sequence diagram illustrating operation by the host system of the operational sequence for various communications with the processing laboratories.

To describe an exemplary embodiment of communications between the processing laboratory 802 and the host system 850 in greater detail, FIG. 15 illustrates a sequence diagram of the functions which may occur at the host processor 860 when the user is not specifically requesting functions to be performed by the communications system, but instead may be performing other functions at the host processor 860. With reference to FIG. 15, with the communications system at the host processor 860 active, the host "receiving" sequence will include a periodic monitoring of the modem 852 for reception of data from a processing laboratory 802. As shown in FIG. 15, if signals from the modem 852 indicate that a communications connection has been established from a particular processing laboratory 802, the host communications system will interrupt primary execution of the functional operation of the host processor 860. Concepts associated with interrupt operation of a processor execution are well known in the art and will not be described in detail herein.

It is preferable at the time of the interrupt to indicate to the user operator that such an interrupt has occurred and that the processor 860 will perform functions in accordance with data signals received from the densitometer 210 through the modem 852 of the host system 850. For example, with the host processor 860 including a visual display monitor, a "window" can be generated on the display monitor with appropriate information indicating that communications are occurring with a densitometer 210 of a processing laboratory 802. In this regard, and as shown in FIG. 15, the visual display can include data expressly identifying the specific processing laboratory 802 currently communicating with the host system 850. This information can be obtained from appropriate data signals transmitted from the densitometer 210 of the specific processing laboratory 802 which has established communications with the host system 850. That is, each processing laboratory 802 can have a specific identification number or other appropriate data distinguishing the individual processing laboratories 802.

In addition to identifying the specific laboratory 802, it is also possible for the host system 850 to visually display to the user the particular communications activity occurring with the processing laboratory 802. That is, the data signals transmitted from the densitometer 210 can preferably include a data code selectively indicating the particular function to be performed by the communications interaction between the processing laboratory 802 and the host system 850. For example, such an activity may include the transmittal of color measurement data from the densitometer 210 to appropriate memory storage of the host processor 860.

In addition to providing an indication of the particular laboratory 802 and the activity or function being performed by the communications system, it is also possible to provide other "quality control" information to the user. For example, it is possible for the host processor 860 to generate an appropriate visual display indicating the latest detected "error" occurring with respect to communications transmission. In addition, for purposes of ensuring that communications transmission is being maintained at an appropriate quality level, it is also possible for the system to obtain and display a count of, for example, the total number of errors occurring during this particular communications sequence. It is apparent that other information may also be displayed to the user operator relating to the status and particular functional activities being undertaken with respect to communications with the densitometer 210.

Following the display of appropriate informational data to the user operator, and further following completion of the communications with the processor laboratory 802, appropriate signals can be established indicating to the host processor 860 that all functional activities related to this communications "session" have been completed. Following such completion, control of functional execution of the host processor 860 can be returned to the execution sequence which was occurring at the time of the interrupt. As with the concepts associated with interrupt generation and sequencing, concepts associated with the return of control to primary execution sequences following interrupts are well known in the art and are not described in detail herein.

With respect to communications sequence executions at the user operator level, and as previously mentioned herein, various options can be provided to the user operator. As previously described, one of the activities which the user operator may wish to undertake at the host system 850 is to obtain color measurement data from the densitometer 210 at a particular processing laboratory 802. In this regard, the network 800 may be configured such that each of the processing laboratories 802 is "required" to submit color measurement "activity" report data periodically on a relatively fixed schedule. The user at the host system 850 may wish to have the option to review laboratory data from specific ones of the processing laboratories 802 which has been previously received through the communications system. With respect to particular "sub-options" which may be made available to the user, it may be preferable to allow the user to select for analysis only the color measurement data which has been most recently received from a particular laboratory. Still further, if each of the laboratories 802 is essentially "required" to provide color measurement data on a periodic basis, the information provided to the user operator can include informational data relating to those processing laboratories which have not transmitted color measurement data on a timely basis.

Further, with respect to analysis of color measurement data, various thresholds can be established with respect to limitations on color quality, such as various optical densities and the like. It is possible for the communications system and the host processor 860 to include functional sequences which identify those processing laboratories for which such color measurement thresholds have been exceeded. In this manner, it is possible to specifically identify those processing laboratories 802 for which modifications are necessary with respect to the color processing of the film or paper processing apparatus 804. Still further, and as previously mentioned, it is possible for the report data to be selectively generated to the visual display monitor of the host processor 860 or, alternatively, to be applied to a peripheral device such as a printer 862 through communications line 864. It will be apparent to the user that various other sub-options can be associated with obtaining and analyzing color measurement data received from the laboratories 802.

With respect to other options available to the user operator at the host system 850, the communications system can include the capability of transmitting various data from the host system 850 to each of the densitometers 210 of each of the processing laboratories 802. For example, the options available to the user operator at the host system 850 can include the option of transmitting a data message to be displayed on the display 490 of a densitometer 210 associated with a particular laboratory 802. Still further, other "message transmissions" can be made available as options to the users, whereby messages which may be of greater length or size then the display 490 can be transmitted to a particular densitometer 210. Still further, as a sub-option with respect to message transmission, the system can be configured so that the user can provide not only informational data regarding the particular laboratory 802 to which the message should be transmitted, but can also provide information regarding a date and time for display or availability of the message to the particular densitometer 210. For example, the user operator at the host system 850 may wish to provide a message to a particular laboratory 802 which is to be made available to laboratory 802 only after a particular date and time. The communications system can be configured so that such a message will not be transmitted from the host system 850 to the densitometer 210 until such date and time has occurred.

Still further, and as described in the previously referenced Cargill et al patent application, various data may be stored within each of the densitometers 210 with respect to color measurement analysis of control or reference strips. Such data to be stored in each of the densitometers 210 can be modified by transmitting new data from the host system 850 to selected ones of the densitometers 210.

As apparent to the user, numerous other functions can be associated with the transmission of data from the host system 850 to the processing laboratory 802. For example, and as described in somewhat greater detail herein, data from the host system 850 may be desired to be generated and applied to a peripheral device associated with the densitometer 210 at a particular processing laboratory 802. In this regard, and with respect to FIG. 13, it is possible that the communications line 806 connected to port A of the densitometer 210 may be interconnected to a device such as a printer or the like. The host system 850 can have the capability of directly transmitting data to the printer interconnected to port A through the use of a "pass through" option, whereby the incoming data from the host system 850 is applied to port B and is then essentially directly transmitted through port A to the peripheral device connected to communications line 806. Various other potential options associated with communications between the densitometer 210 and the host system 850 are described in subsequent paragraphs herein with respect to FIGS. 21 and 22.

The foregoing description has essentially comprised details associated with functional operation of the communications network 800 with respect to the "user interface" level. Details associated with the actual functional operations of intercommunications between remotely located devices through telecommunications lines are relatively well known in the art. Such details are typically referred to as network "protocols." Accordingly, a detailed description of all functional activities required for establishing and maintaining such communications transmissions and receptions will not be described in detail herein. Instead, a basic exemplary description is provided in the following paragraphs.

Figure 16A:
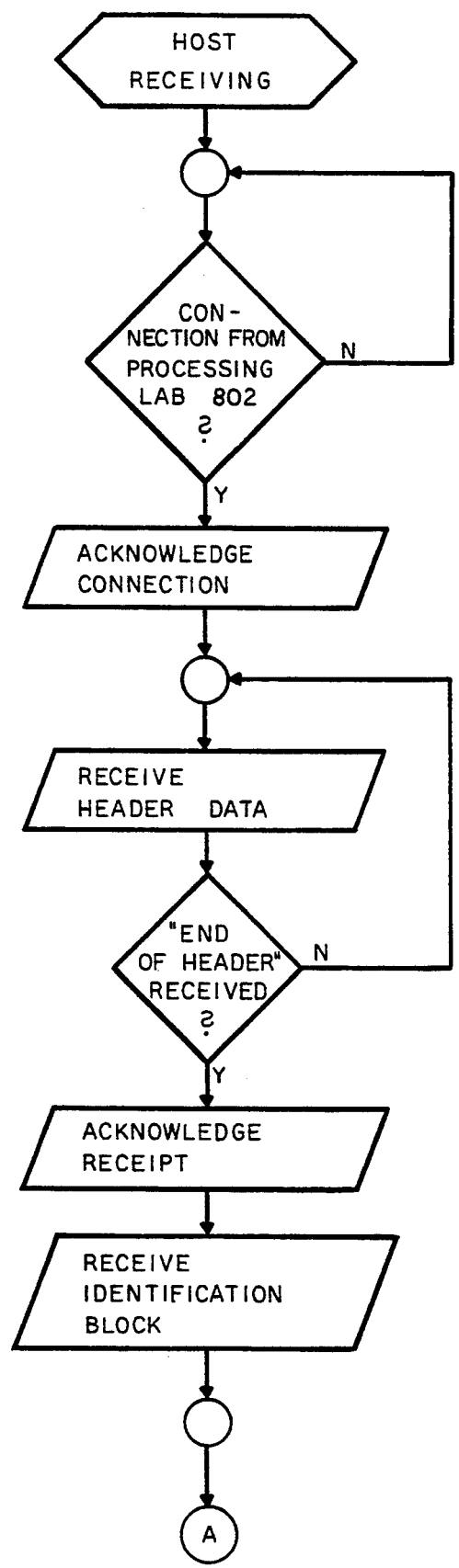
FIG. 16a and 16b a functional sequence diagram illustrating functions associated with the performance of job sequences by the host system.
Figure 16B:
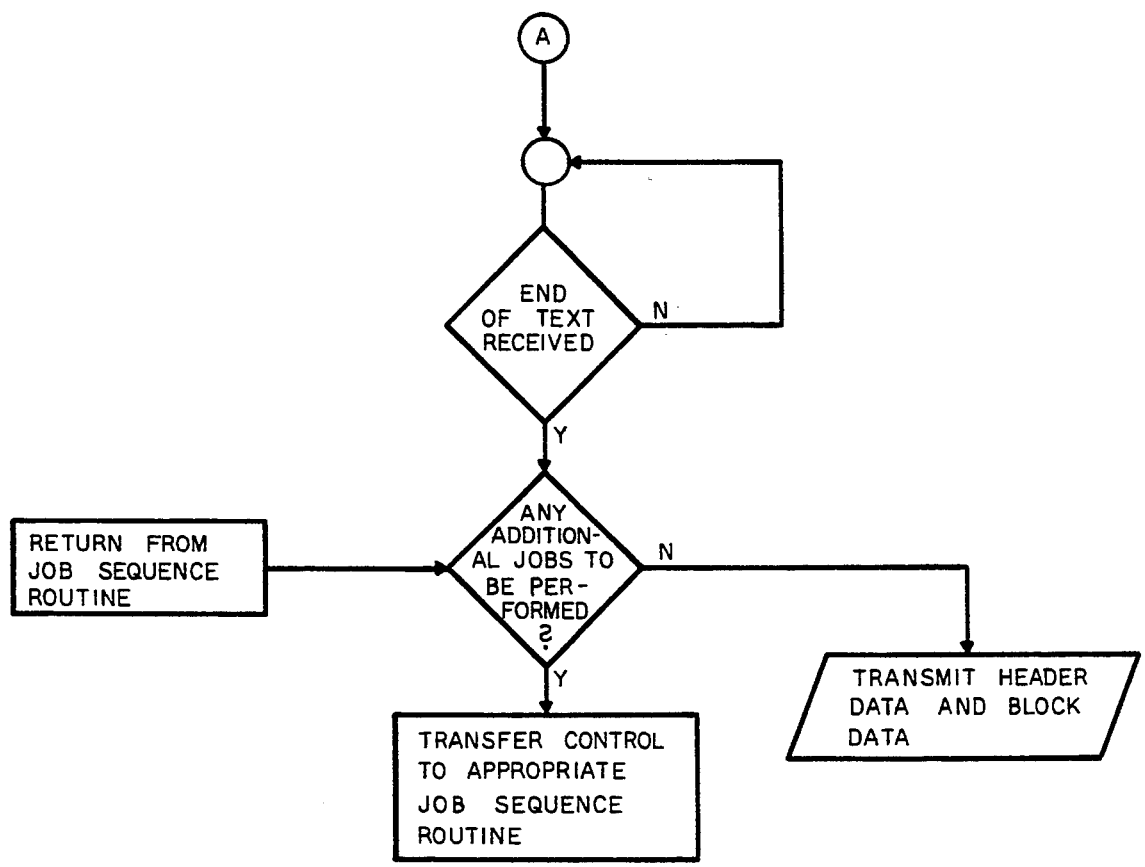

In a communications arrangement such as that shown in the network configuration 800, it is possible for actual initiation of a communications "session" to always be initiated from a particular system of the configuration. For example, in the communications network 800 with respect to intercommunications between the processing laboratories 802 and the host system 850, it is possible for the network protocol and other communications functions to be established such that the densitometers 210 of each of the processing laboratories 802 actually initiate each communications session. In this regard, FIG. 16 illustrates an exemplary sequence diagram associated with the establishment of a communications session and commencement of a particular functional operation at the host system 850. For purposes of description, each of the available functional operations associated with communications between the processing laboratories 802 and the host system 850 are described herein as "jobs" or "job sequences."

With reference again to FIG. 16, with the host processor 860 operating in a mode such that communications with the processing laboratories 802 can be established, the host processor 860 can periodically monitor the communications line 858 so as to determine if a communications connection has been established through the modem 852 from a particular processing laboratory 802. When and if such a communications connection has been established from a processing laboratory 802, the host processor 860 can be made to transmit appropriate "acknowledgement" characters to the interconnected densitometer 210. Such acknowledgement characters can provide an indication to the functional operational sequences of the densitometer 210 that the host processor 860 is "ready" to receive appropriate data transmitted from the densitometer 210. After such an acknowledgement has been received from the host processor 860 at the densitometer 210, data signals in the form of a "job header" can be transmitted from the densitometer 210 to the host processor 860. For example, such data signals can include signals representative of characters indicating a "start of header" is being transmitted. Such a job header can include data signals which provide various control information associated with the particular job sequence to be performed. For example, the signals associated with the job header can indicate the particular job sequence to be performed, the number of data blocks which may be associated with the particular job sequence and the length of the data blocks to be transmitted. Still further, such control information can include informational data regarding whether any additional job sequences will be transmitted from the densitometer 210 after a response has been received from the host system 850, and can also include information regarding when and if the communications established between the densitometer 210 and the host system 850 should be discontinued.

Following receipt of the job header data signals, the host system can continually monitor for receipt of an "end of header" character. Until such time as such an appropriate character signal has been received, data received by the host processor 860 will be characterized as header informational data. Following receipt of the end of header character, it is possible for the host system to transmit further acknowledgement signals indicating receipt of the header information.

After the header information has been received, and if this particular function is the "first" job sequence to be performed after a communications connection has been established, an "identification block" of data signals can be transmitted from the densitometer 210 to the host processor 860. Such an identification block can include various information regarding the densitometer 210 of the particular laboratory 802 establishing communication. For example, this identification block can include informational data regarding the particular laboratory 802 establishing communication, a model number of the particular densitometer 210 associated with the laboratory 802, current date/time and similar information. Such information can be used in part as previously described in displaying data to the user operator regarding the particular laboratory 802 which has established communication.

With the transmission of the identification block of data signals, the host processor 860 can continuously monitor for receipt of an "end of text" character indicating completion of the transmission of the identification block. When such a character has been received, the functional operational sequence of the host processor 860 can determine if any particular job sequences are to be performed at this time. If no additional functional operational sequences are to be performed, the host processor 860 can transmit the appropriate header and block data to the densitometer 210 indicating that the communications connection should be discontinued. If additional job sequences are to be performed, sequential operational control can be transferred to the particular operational sequence for performance of the appropriate job sequence routine. After a job sequence routine has been completed, a return from such a routine can be made so as to further determine if any additional job sequences are to be performed.

Figure 17:
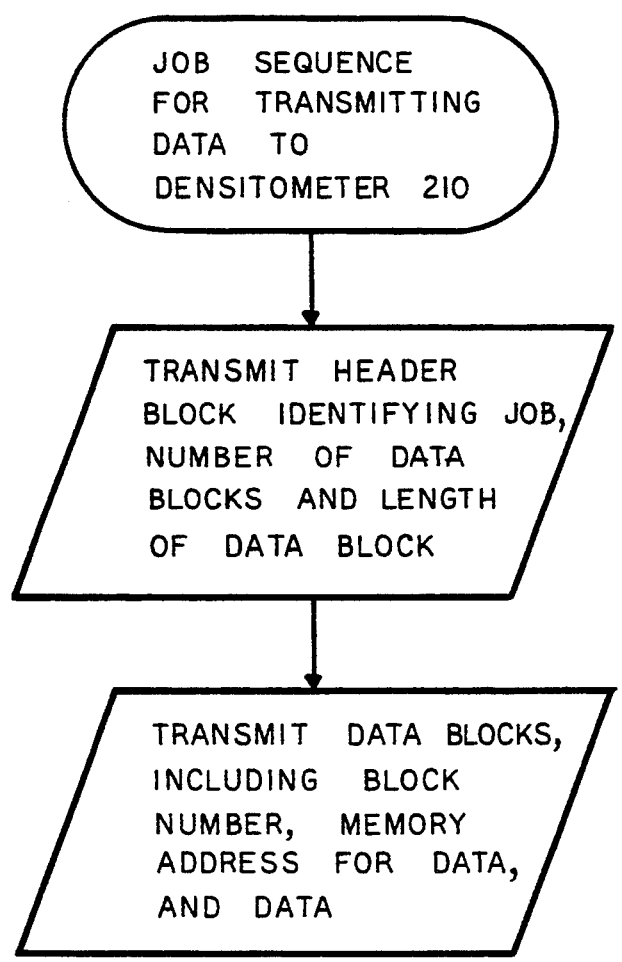
FIG. 17 is a functional sequence diagram illustrating a job sequence for transmitting data to a densitometer of a processing laboratory.

As earlier described, this type of communications arrangement can include various desired job sequences associated with communications of data between the densitometer 210 and the host processor 860. For example, FIG. 17 illustrates in relatively simple block diagram format a job sequence associated with the transmission of data from the host processor 860 to the densitometer 210. For such a job sequence, data signals representative of a header block can first be transmitted to the densitometer 210 after communications have been established through the modems 808, 852 and the communications line 822. This header block can include data signals indicating the particular type of job sequence currently being performed, along with information regarding the particular number of blocks of data to be transmitted from the host processor 860 to the densitometer 210. In addition, informational data such as the length of the data blocks can also be transmitted to the densitometer 210.

Following transmission of the header block data information, the actual data blocks can be transmitted. For purposes of data block transmission, each block can include a particular data format as desired. For example, each data block can be in the form of including a set of data signal characters indicative of the block number. In addition, if this data is to be transmitted to a particular memory location of the densitometer 210, the data block format can include a particular memory address of the memory 746 of the densitometer 210 for storage of the forthcoming data. Following information regarding the block number and the memory address, the appropriate data can be transmitted for storage in the memory 746 of densitometer 210. With such transmission, appropriate start of text, end of text and acknowledgement characters can also be communicated between the host processor 860 and the densitometer 210.

Figure 18:
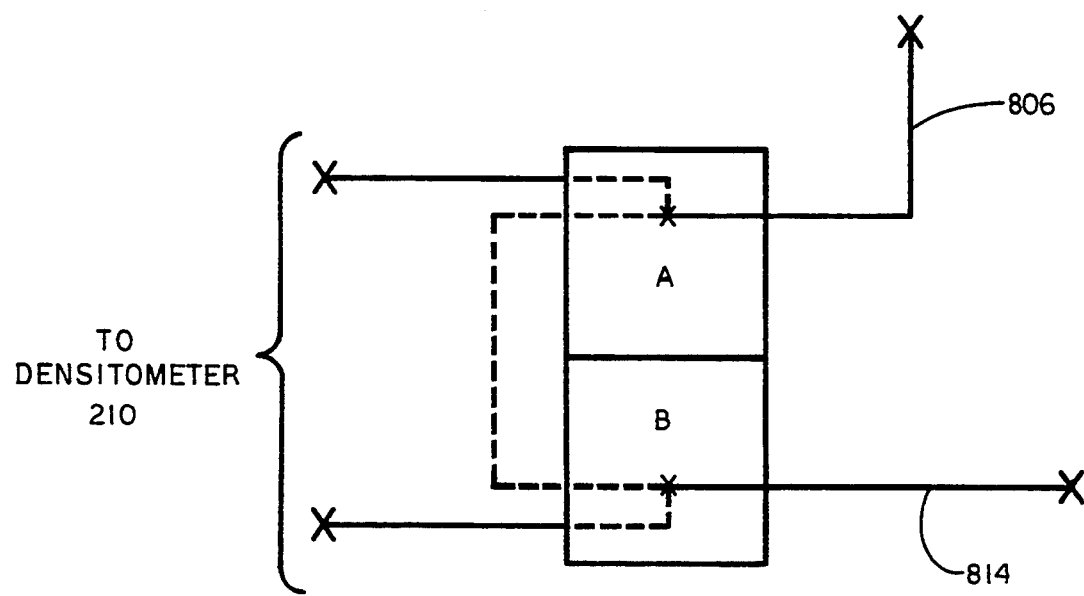
FIG. 18 is a symbolic representation of a switching arrangement for ports A and B for use of the network in a pass through mode.
Figure 19:
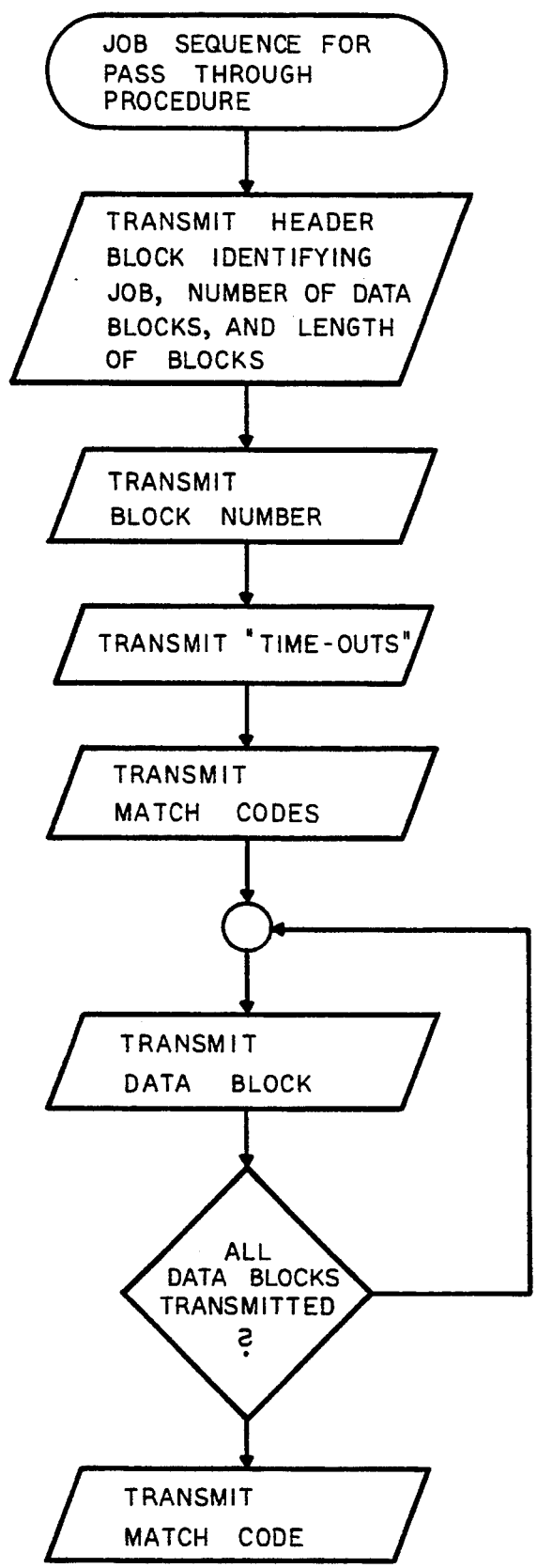
FIG. 19 is a functional sequence diagram of an operational sequence within the host system for transmission of data in the pass through mode.

With respect to other exemplary job sequences which may be performed with respect to communications between the processing laboratories 802 and the host system 850, and as earlier described herein, the job sequences can include transmission which is essentially directly from the host processor 860 to devices associated with the film or paper processing apparatus 804 of a laboratory 802. In this regard, the job sequences can include a "pass through" option for the densitometer 210. FIG. 18 illustrates a symbolic representation of such a pass through option. In this regard, the ports A and B of the interface 544 can essentially be functionally "switched" so as to provide a direct interconnection between the communications line 806 and the communications line 814. Accordingly, data transmitted from the host processor 860 to the densitometer 210 through communications line 814 and port B can be directed through port A and transmitted to an appropriate peripheral device on communications line 806. With respect to actual realization of such a pass through procedure, FIG. 19 illustrates a job sequence within the host processor 860 for performance of such a pass through procedure. As shown in FIG. 19, after communications have been established with a particular laboratory 802, an appropriate header block can be transmitted to the densitometer 210, identifying the particular job sequence (in this case, a pass through procedure), the number of data blocks to be transmitted and the length of the data blocks. For purposes of this type of transmission, the host processor 860 can transmit information regarding the block number of the data block as previously described with respect to a conventional transmission of data to be stored in memories of the densitometer 210. However, in addition, the host processor 860 can also transmit informational data signals in the form of "time out" characters. The time out characters can identify, for example, the maximum time between transmission of data blocks which should be "allowed" by the densitometer 210. That is, with respect to functional operation of the densitometer 210, after a data block has been received from the host processor 860, a clock time can be initiated by the densitometer 210. If an additional data block is not received within the period of time specified by the time out characters, the densitometer 210 can be made to discontinue the communications connection with the host processor 860.

In addition to the block number and time out characters, the host processor 860 can also generate a "match code" comprising data signals which should be monitored by the densitometer 210 so as to determine when the pass through procedure is complete and the densitometer 210 should again resume "control" of the communications session. With respect to functional operation at the host processor 860, the host processor 860 would then transmit the appropriate data blocks, while continuously monitoring for a determination as to whether or not all appropriate data blocks have been transmitted. After all appropriate data blocks have been transmitted, the host processor 860 is then made to transmit an appropriate match code for indication to the densitometer 210 that transmission on a pass through basis has been completed.

With respect to functional operation within the densitometer 210, after a data block has been actually received by the densitometer 210, the data associated with the data block is then transmitted through the interface 544 to port A and communications line 806 within the processing laboratory 802. Such a pass through transmission will continue until the densitometer 210 receives a data block segment having a match code corresponding to the match code indication data originally transmitted to the densitometer 210. After receipt of such a match code, the densitometer 210 can then resume control of the communications session.

Figure 20:
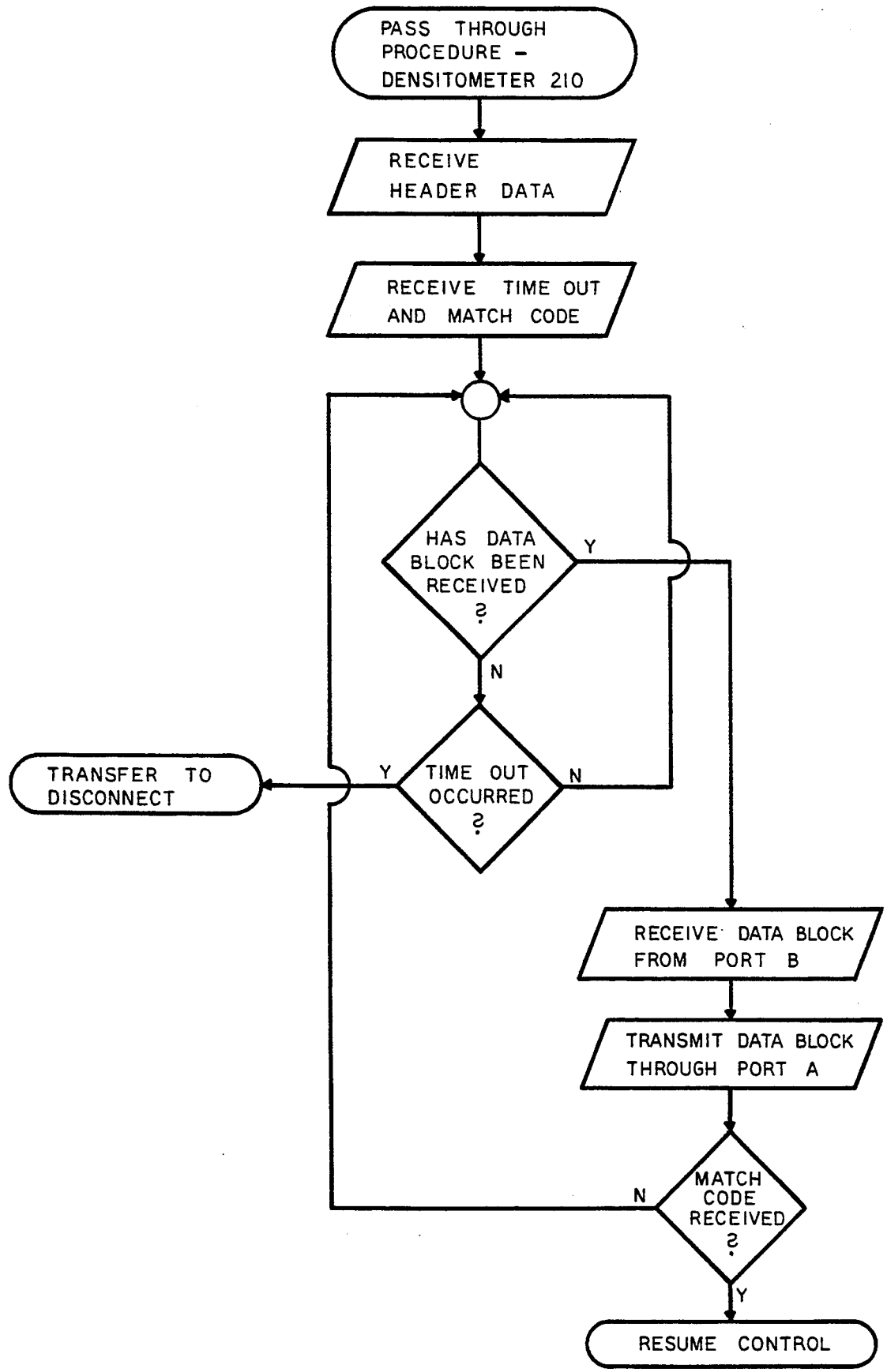
FIG. 20 is a functional sequence diagram of an operational sequence for the densitometer during operation in a pass through mode.

With respect to the functional operation within the densitometer 210, FIG. 20 illustrates a sequence diagram for such operation. As earlier described, after the densitometer 210 receives the appropriate header data, informational data regarding the "time out" and match code is also received. The densitometer 210 will then monitor for receipt of an appropriate data block. When the monitoring indicates that a data block has not yet been received, the densitometer 210 will also monitor the clock time so as to determine if the maximum time between data blocks has been exceeded. If the maximum time has been exceeded, functional sequence operation can be transferred to a disconnect procedure so as to discontinue the communications session with the host processor 860. Assuming that a time out has not occurred, and a data block has been received from port B on communications line 814, the data block is transmitted through port A of the interface 544 to the communications line 806. With respect to each of the data blocks, a determination is also made as to whether a data block segment includes a match code. As also earlier described, if a match code has been received, the densitometer 210 again resumes control of the communications session and the pass through of data from the host processor 860 to port A is discontinued. If a match code has not been received, monitoring by the densitometer 210 continues for receipt of data blocks.

Figure 21:
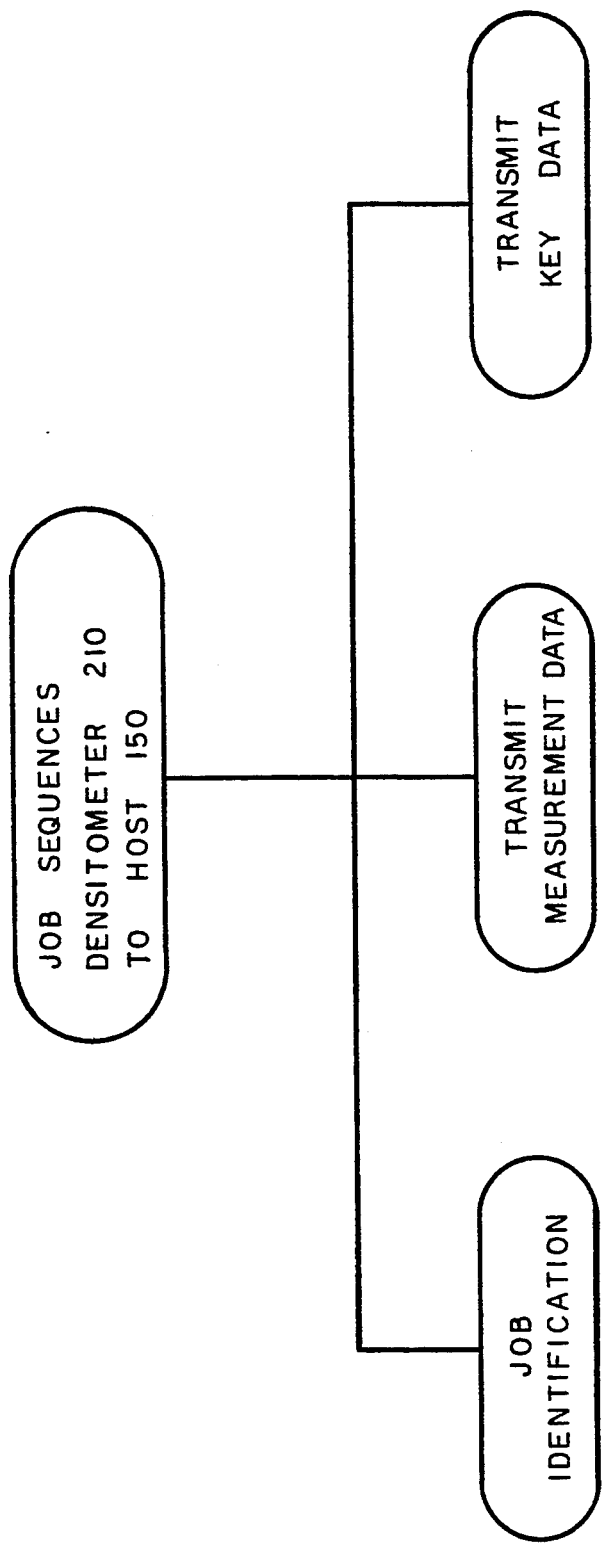
FIG. 21 is a block diagram illustrating alternative job sequences which may be performed with respect to the transmission of informational data from the densitometer to the host system.

The foregoing has described the general communications functions and general concepts associated with a network protocol for communications between the processing laboratories 802 and the host system 850. As earlier described, various types of job sequences can be included within the communications functions. For example, FIG. 21 illustrates a particular set of job sequences associated with transmission of informational data from the densitometer 210 to the host system 150. Such job sequences can include a job identification sequence as earlier described, whereby information is transmitted from the densitometer 210 to the host system 150 regarding general informational data associated with the communications session, such as the identification of the particular processing laboratory 802 to which communication has been established, a model number of the densitometer 210 and similar information.

In addition, the job sequences associated with transmission of data from densitometer 210 to the host system 150 can include the transmission of measurement data associated with color quality measurements made by the densitometer 210 with respect to the film or paper processing apparatus 804. Still further, the job sequences can include the transmission of data from the densitometer 210 to the host system 850 representative of data input by a user at the densitometer 210 through the keys 492. For example, after such a job sequence has been initiated, the densitometer 210 can be made to transmit to the host processor 860 data signals in the form of characters representative of particular keys of the keys 492 as depressed by the user at the densitometer 210.

Figure 22:
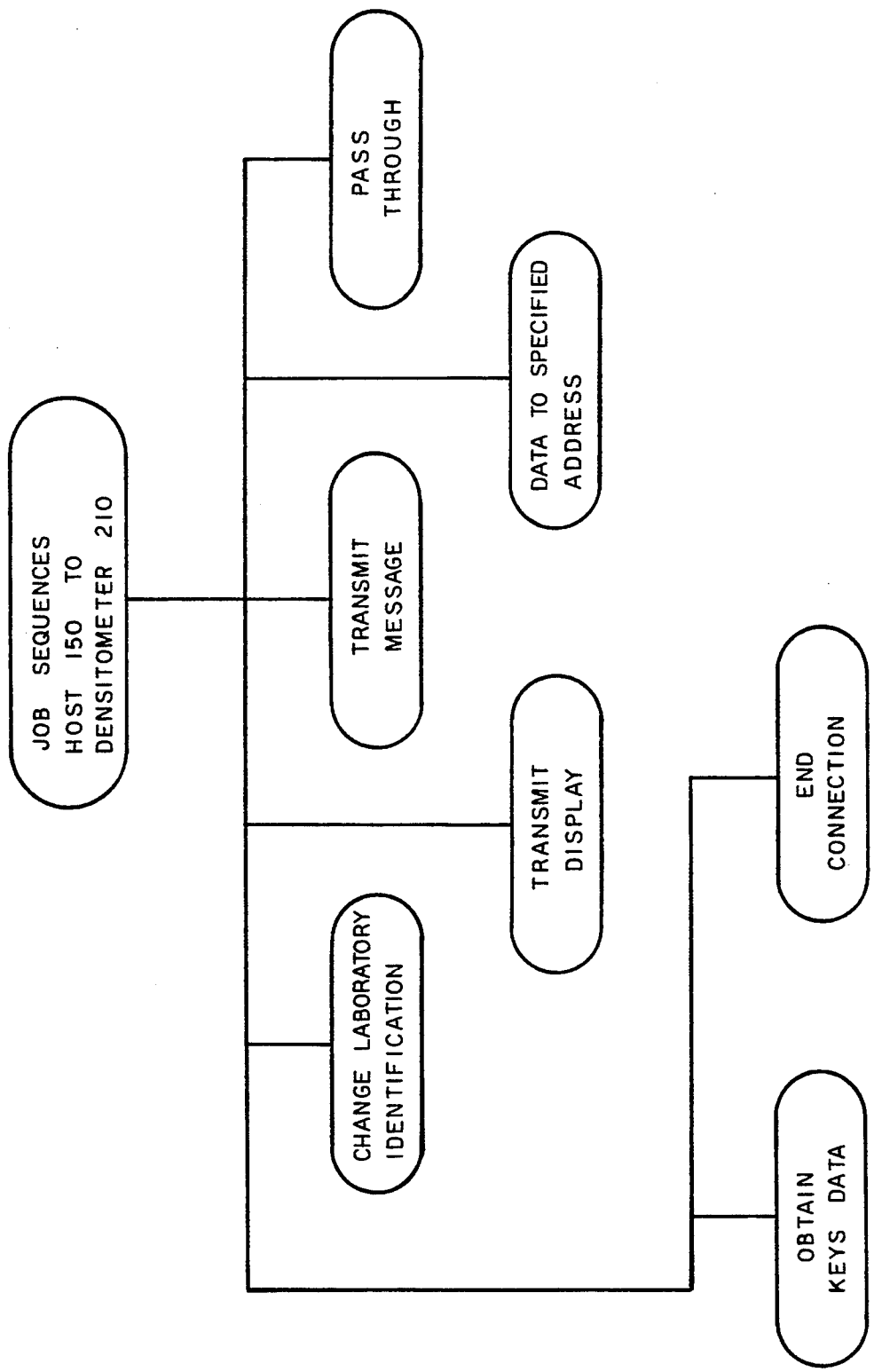
FIG. 22 is a block diagram illustrating alternative job sequences which may be performed with respect to the transmission of data from the host system to the densitometer.

FIG. 22 illustrates potential job sequences associated with transmission of data from the host system 150 to the densitometer 210. For example, and as expressly shown in FIG. 22, such job sequences can include a job sequence for allowing a user operator at the host system 150 to modify the identification number or characters for a particular laboratory 802. Further, the job sequences can include a "transmit display" sequence, whereby data signals transmitted to the densitometer 210 will be displayed on the visual display 490. In a somewhat similar manner, and as previously described herein, the host system 150 can transmit a data message to the densitometer 210. The densitometer 210 can be made to store the data message in a buffer or similar memory for purposes of display on the visual display 490 at a later time. Still further, and as previously described herein, the host system 150 can transmit data to the densitometer 210 for purposes of storage in specific memory addresses of the memory 746 of densitometer 210. Also as previously described herein, the job sequences can include the transmission of data from the host system 150 to the densitometer 210 for "pass through" to devices associated with port A and communications line 806.

Other job sequences related to transmission of data signals from the host system 150 to the densitometer 210 can include request sequences for certain functions to be performed. For example, a job sequence can include a "request data" sequence, requesting the densitometer to return the transmission of data previously acquired and stored in the densitometer 210. Such a request for data can include various sub-options, including, for example, a request only for data acquired by the densitometer 210 prior or subsequent to a particular date and time. Another job sequence in the form of a request for data can include a request for the transmission of data signals indicative of keys of the keys 492 as depressed by the user at the densitometer 210. Finally, another job sequence to be performed by the host system 150 can include the transmission of appropriate signals to the densitometer 210 indicating that the communications session should be discontinued and the communications connection should be ended.

With respect to prior art systems for various types of communications between remotely located systems, such systems were often substantially "device dependent" whereby a substantial amount of information was necessary to be known by the receiving device with respect to the particular device from which data was being received. For purposes of providing a substantially open format and a substantially device independent network configuration, and in accordance with the invention, the communications arrangement previously described herein with respect to the processing laboratories 802 and the host system 50 of the network configuration 800 can include an "open format" configuration whereby each of the densitometers 210 is capable of accepting device independent data from a variety of equipment devices within the processing laboratory 802, for purposes of subsequent transmission to the host system 850. In addition, data messages or other data from the host system 850 can be accepted and stored within the memory 746 of the densitometer 210 for purposes of subsequent display to the densitometer user or, alternatively, subsequent transmission to other apparatus within the processing laboratory 802. For this type of arrangement, a specific block of the random access memory 746 of each of the densitometers 210 is "reserved" as a "log" for use in communications among the densitometer 210, other apparatus within the processing laboratory 802 and the host system 850.

Figure 23:
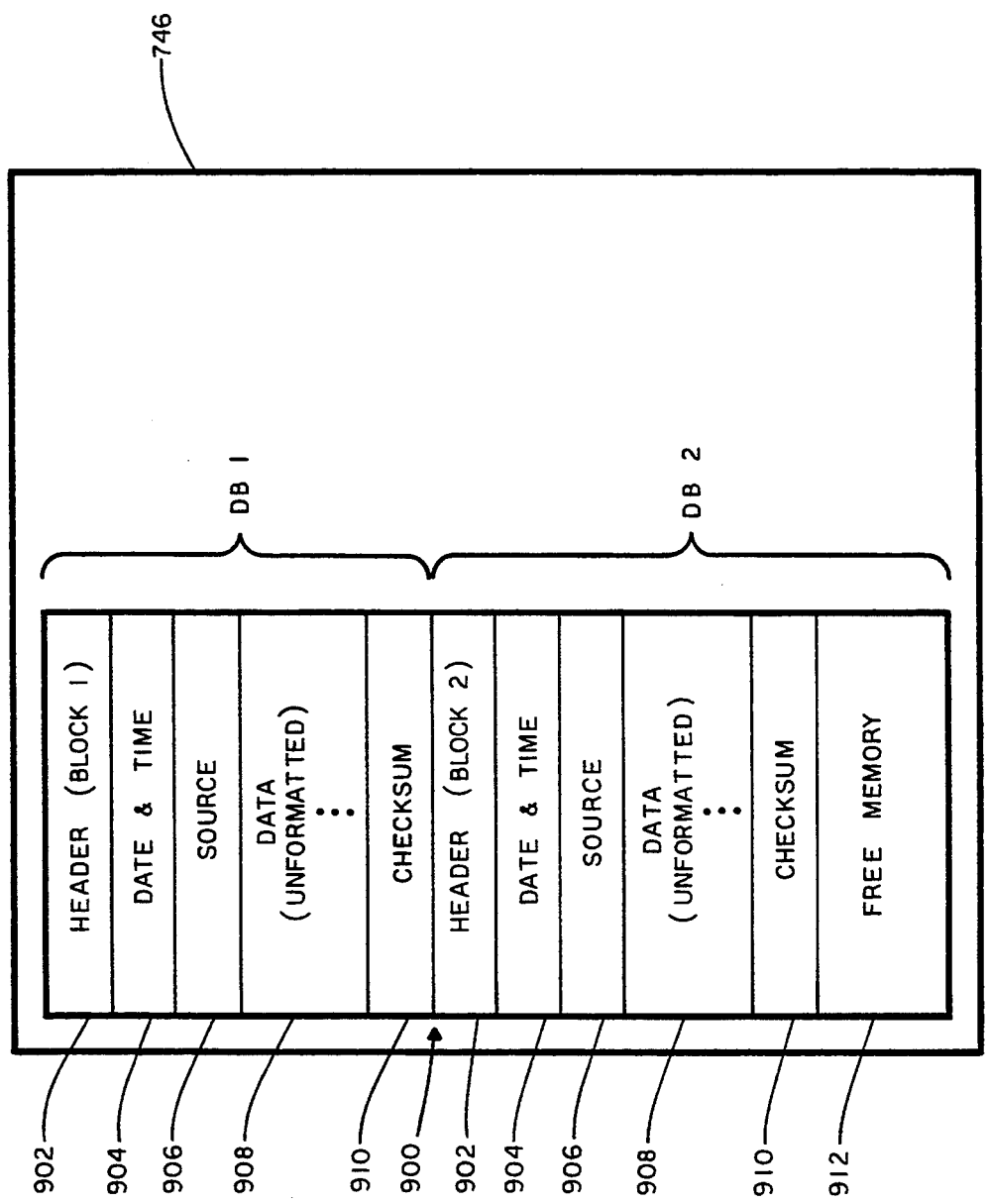
FIG. 23 is an exemplary memory layout for a log buffer memory in accordance with the invention.

FIG. 23 illustrates a configuration of this memory, identified as log buffer memory 900. The log buffer memory 900 is reserved as part of the random access memory 746 of the densitometer 210. Data received by the densitometer 210 is stored in a particular format within the log buffer memory 900 as expressly shown in FIG. 23. For purposes of explanation and as an exemplary embodiment, two data blocks are shown in FIG. 23 as being stored within the log buffer memory 900, and are identified as data block one (DB 1) and data block two (DB 2). Each of the data blocks includes an initial set of bytes in fixed length format identified as the header segment 902. In addition, following each of the header segments 902, each data block includes a fixed length segment identified as a date and time segment 904. Within each of the data blocks following the header segment 902 and date and time segment 904 is another fixed length memory segment identified as the source segment 906. Following the source segment 906, each of the data blocks includes a variable length memory area in which unformatted data can be stored, and is identified as the data segment 908. At the end of each data segment 908 is a segment identified as the checksum segment 910. As further shown in FIG. 23, each of the data blocks is stored within the log buffer memory 900 in a contiguous sequence, so that unused area of the log buffer memory 900 appears at the end of the buffer memory 900 and is illustrated in FIG. 23 as free memory 912.

Figure 24:
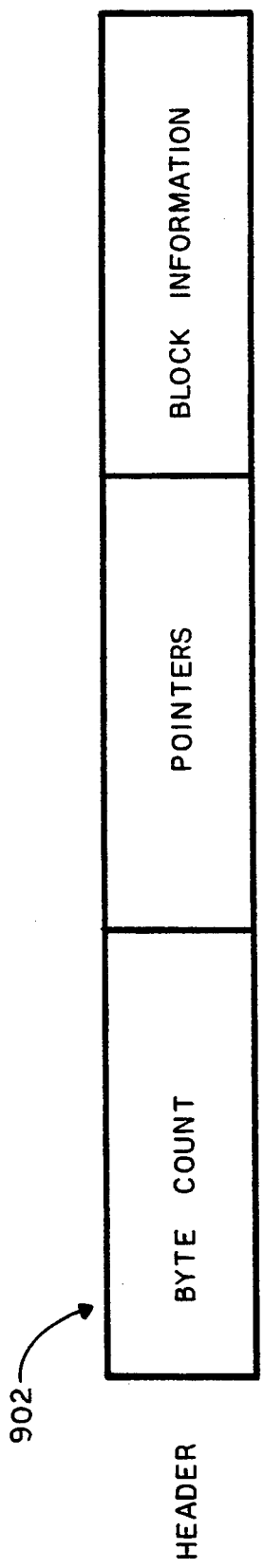
FIG. 24 is an exemplary byte layout for the header segment of the log buffer memory shown in FIG. 23.

FIG. 24 illustrates an exemplary embodiment of the format of the header segment 902 for each of the data blocks. The header segment is a fixed length segment providing various informational data about the data block. For example, as illustrated in FIG. 24, the header segment can include a byte count portion indicating the actual length of the data stored within the particular data block. Correspondingly, the header segment 902 can also include informational data such as a "pointers" section which may indicate actual memory addresses (or relative memory addresses) for start/end of data, and similar information associated with describing the particular block. In addition to a pointer section and a byte count section, the header segment can also include other bits indicating other desired information regarding the block, with these bits being identified in FIG. 24 as the "block information" bits.

With respect to the date and time segment 904, this segment can also be a formatted field included within each of the data blocks. The field should preferably be fixed length and includes information indicating a date and time at which this particular data block was transmitted to and stored within the memory 746 of the densitometer 210. The data associated with the date and time can be obtained from a conventional clock associated with the processor 654 of the densitometer 210. For purposes of efficient use of the log buffer memory 900, when a data block is transmitted from the log buffer memory 900 to another device such as the processor 860 of the host system 850, the date and time segment 904 can be transmitted with the appropriate data. Conversely, the header segment 902 is a segment substantially for internal functional operation of the densitometer 210 and need not be transmitted with the other information associated with the data block.

Figure 25:
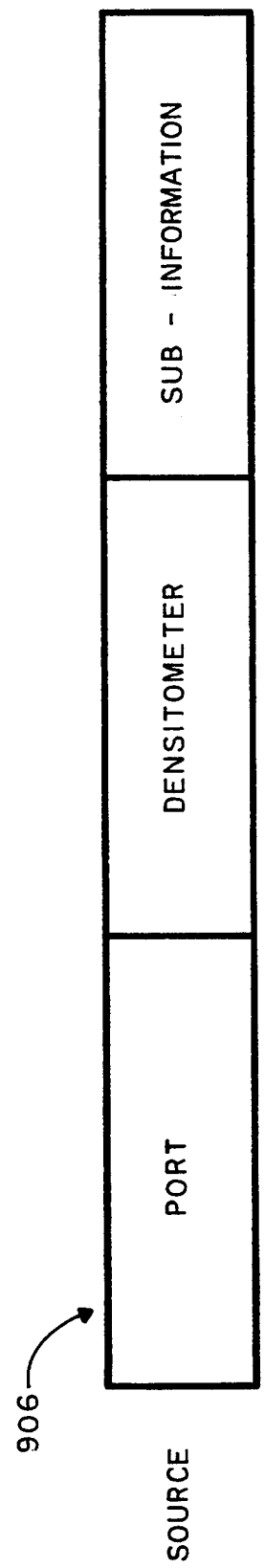
FIG. 25 is an exemplary memory layout for the source segment of the log buffer memory shown in FIG. 23.

FIG. 25 illustrates an exemplary format for the source segment 906. The source segment 906 is preferably of a fixed length format and can include various information regarding the original transmission of the data to the densitometer 210. For example, as further shown in FIG. 25, the source segment 906 can include bytes identified as the "port" section, expressly identifying whether the data associated with the data block was received through port A of the densitometer 210 or, alternatively, through port B of the densitometer 210. Correspondingly, the source segment 906 can also include bits identified as the "densitometer" bits, indicating that the data was originally formatted and initiated through input directly at the densitometer 210.

Still further, the source segment 906 can include other bytes identified in FIG. 25 as the "sub-information" bytes, providing further information associated with the original transmission of the data to the densitometer 210. For example, and as described in subsequent paragraphs herein, the sub-information bytes can describe the particular mode of transmission of the data to the log buffer memory 900. A more detailed description of exemplary modes is set forth in subsequent paragraphs herein.

As described with respect to FIG. 23, following each of the source segments 906, the log buffer memory 900 will include unformatted data in variable length format as received by the densitometer 210. At the end of each unformatted variable length block of data 908 is preferably the checksum segment 910. Such a checksum segment 910 can be an additive or similar checksum of the header segment 902, date and time segment 904 and source segment 906. Such a checksum is for purposes of insuring data integrity and is preferably used only internally by the densitometer 210 so as to ensure appropriate formatting and transmission.

Transmission of data to be stored within the buffer memory 900 can be provided such that each data block within the log buffer memory 900 is essentially "written" to the buffer memory 900 commencing at a memory address immediately following a checksum of a prior data block. To maintain an open format and for purposes of simplifying procedures, when the free memory 912 is essentially "used up", new data being transmitted to the log buffer memory 900 of the densitometer 210 can be written into the memory 900 in a circular buffer manner, whereby the "oldest" data is overwritten with new data commencing at the beginning of the buffer memory 900 area.

With the log buffer memory 900, and in accordance with the invention, the buffer memory 900 is accessible through both port A and port B of the densitometer 210. Various protocols or interface communication sequences can be utilized for purposes of transmitting data from the log buffer memory 900 and receiving data into the log buffer memory 900. For example, for purposes of the densitometer 210 receiving data into the log buffer memory 900 from other devices within the processing laboratory 802, port A of the densitometer 210 can be employed, along with communications line 806. As an example of an interface protocol to be utilized for such transmission, the particular device of the processing laboratory 802 which desires to transmit data to the log buffer memory 900 can initially transmit a communications command indicative of the desired communications activity. In addition, the communications command can also include an appropriate representation of a "terminator" character. Following reception of the command by the densitometer 210, the functional operational sequence of the densitometer 210 can essentially enter into a "wait" mode. In this mode, characters received through port A in a serial manner can be sequentially stored in the log buffer memory 900. However, the densitometer 210 will also interrogate each of the received data characters to determine if any of the characters correspond to the terminator character. After the terminator character is received, the functional operational sequence of the densitometer 210, with respect to receipt of serial data from the device within the processing laboratory 802, is discontinued. Thereafter, the appropriate data can be formatted within the header 902, date and time segment 904 and source segment 906 for the received data. It should be emphasized that with this type of memory buffer format and communications through port A, it is unnecessary for the densitometer 210 to obtain any specific data regarding the actual device from which data is being transmitted.

Another arrangement for entering data blocks into the log buffer memory 900 includes communications by a user of the densitometer 210 through the keys 492 illustrated in FIG. 12. In this configuration, a particular key of the keys 492 can be determined to be an informational data key indicative of the desire of the user operator to enter data into the densitometer 210 for storage in the log buffer memory 900. The user operator can also enter information through the keys 492 indicative of the particular terminator character to be monitored by the densitometer 210. After entry of appropriate informational data by the user operator, the densitometer 210 can again enter a functional operational sequence essentially comprising a "wait" mode. In this mode, data characters received through communications line 806 and port A can be stored in the log buffer memory 900 in a variable length and unformatted field basis. When the terminator character is detected by the densitometer 210, receipt of data through port A will be discontinued.

In addition to receipt of data from equipment devices internal to the processing laboratory 802, the densitometer 210 and the log buffer memory 900 can also be configured so as to provide for receipt of data from the host system 850. Utilizing a communications arrangement and network protocol as previously described herein, informational data signals can be transmitted from the remote host system 850 to the densitometer 210 indicating that the data is to be transmitted to and stored within the log buffer memory 900. Following the receipt of such data signals, further information transmitted from the host system 850 will be received through port B and stored within the log buffer memory 900 as previously described herein with respect to transmission through port A. Correspondingly, when communications connections have been established with the host system 850, data previously stored within the log buffer memory 900 can be transmitted to the host system 850 through port B of the densitometer 210. A communications arrangement or protocol for the transmission of such informational data can be established in the manner previously described herein with respect to other communications functions between the processing laboratory 802 and the host system 850.

In addition to the foregoing functions, data transmitted from the remote host 850 and stored within the log buffer memory 900 can also be made available by appropriate communication commands to be displayed by the user on the display 490 of the densitometer 210. Alternatively, such information can also be transmitted through the serial port A and communications line 806 to other devices within the processing laboratory 802. As also previously described herein, the host system 850 can have the capability of transmitting appropriate commands to the densitometer 210 so as to cause the densitometer 210 to operate in a pass through mode, whereby the host system 850 can essentially control other devices within the processing laboratory 802.

In general, the log buffer memory 900 provides a "time-tagged" log buffer within a communications system utilizing the dual port structure employing ports A and B of the densitometer 210. In this manner, an efficient means of communication can be established between equipment within the processing laboratory 802 and the remote host system 850. In addition, the log buffer memory 900 provides the densitometer 210 with the capability of essentially accepting "device independent" data from a variety of equipment within the processing laboratory 802, providing a time-tagged label for each data block received, and for queueing such data internally within the log buffer memory 900 for purposes of subsequent transmission to the host system 850 when a communications connection has been established. Still further, and as previously described herein, communication messages from the host system 850 can be stored within the log buffer memory 900 for purposes of subsequent display to the user by means of display 490, or for purposes of subsequent transmission to a printer or similar device through port A of the densitometer 210. In addition, and as previously described in detail herein, the dual port structure comprising ports A and B can be utilized with appropriate communications commands and the log buffer memory 900 so as to provide a pass through mode and a direct control of other equipment within the processing laboratory 802 by the host system 850.

The principles of the network message buffer structure in accordance with the invention are not limited to the specific apparatus or functions described herein. It will be apparent to those skilled in the art that additional modifications and variations of the above-described illustrative embodiment of the invention may be effected without departing from the spirit and scope of the novel concepts of the invention.

The embodiments of the invention in which an exclusive property or privilege is claimed are defined as follows:

1. An apparatus for use in a film or paper processing laboratory and connected for communications to a host system remotely located from said processing laboratory, said apparatus comprising:

a densitometer having light source means for projecting light towards a colored surface of an object sample under test at an angle of illumination relative to said surface;

light receiving means for receiving light rays reflected from said object sample under test at a reflection angle relative to said object sample surface;

detection means within said densitometer connected to said light receiving means for detecting said light rays reflected from said object sample surface and for generating electrical signals representative of spectral characteristics of said object sample surface;

processing means within said densitometer connected to said detection means and responsive to said electrical signals fur generating data representative of said spectral characteristics;

a memory structure of predetermined length having a plurality of data storage locations of predetermined number for storing data received from and transmitted to other apparatus within said processing laboratory and said host system as a series of data blocks of variable length, each of said data blocks comprising a first set of data identifying a time of storage of a corresponding data block in said memory structure;

means for generating and storing said time of storage of said corresponding data block;

at least one secondary port means for receiving data from said other apparatus within said processing laboratory and for storing said received data in said data blocks;

at least one primary port means for transmitting data stored in said data blocks to said host system;

said processing means comprises means for transmitting said series of data blocks received from said other apparatus to said host system through said primary port means in a format consistent with the format in which said data blocks are received from said other apparatus, without said apparatus performing any modifications to the format of said data blocks as received from said other apparatus; and said apparatus does not require an independent or dedicated processor for performing or monitoring communication or control functions associated with transmission of data between said other apparatus within said processing laboratory and said host system.

2. An apparatus in accordance with claim 1 characterized in that:

said secondary port means is further adapted for transmitting data stored in said data blocks to said other apparatus within said processing laboratory; and said primary port means is further adapted for receiving data from said host system and for storing received data in said data blocks.

3. An apparatus in accordance with claim 1 characterized in that said apparatus further comprises means for switching said secondary and said primary primary port means into states whereby data received from said host system at said secondary port means is passed to said other apparatus within said processing laboratory through said second port means without necessitating storage of said data in said memory structure.

4. An apparatus in accordance with claim 1 characterized in that said apparatus further comprises means for switching said secondary and said primary port means into states whereby data received from said other apparatus within said processing laboratory at said secondary port means is passed to said host system through said primary port means without necessitating storage of said data in said memory structure.

5. An apparatus in accordance with claim 1 characterized in that said apparatus further comprises:

means for interrogating data signals representative of data to be stored in said memory structure and transmitted from said other apparatus within said processing laboratory so as to determine when and if a data signal indicative of termination has been received;

means for ceasing storage of data in said memory structure representative of said data signals, upon receipt of said data signal indicative of termination; and an indicating means for receiving a data signal from said other apparatus through said secondary port means, said indicating data signal being indicative of the specific data signal to be considered as indicative of termination during subsequent receipt of data signals from said other apparatus through said secondary port means.

6. An apparatus in accordance with claim 1 characterized in that said secondary port means comprises four serial ports.

7. An apparatus in accordance with claim 1 characterized in that said apparatus comprises:

means responsive to specific data received through said secondary port means from said other apparatus within said processing laboratory for storing subsequently received data in said memory structure, said specific data comprising data representative of an instruction command for instructing said apparatus to enter said subsequently received data into said memory structure, and data representative of an expected termination character;

means for determining when and if any of said subsequently received data corresponds to said termination character; and means for ceasing storage of said subsequently received data in the event of receipt of data corresponding to said termination character.

8. An apparatus in accordance with claim 1 characterized in that said apparatus comprises:

means responsive to user input for storing data indicative of an expected termination character or a time out period;

means for storing data indicating that data subsequently received through said secondary port means from said other apparatus is to be stored in said memory structure until receipt of data corresponding to said expected termination character or until a period of time corresponding to said time out period has elapsed; and said subsequently received data is stored in said memory structure from said other apparatus without the requirement of said apparatus receiving an instruction command from said other apparatus for instructing said apparatus to enter said subsequently received data into said memory structure.

9. An apparatus in accordance with claim 1 characterized in that said apparatus further comprises:

means responsive to user input for storing data indicative of an expected termination character or a time out period corresponding to an elapsed period of time; and means responsive to user input for storing data indicating that data subsequently received through said secondary port means from said other apparatus is to be stored in said memory structure until receipt of data corresponding to said expected termination character, or until a period of time corresponding to said time out period has elapsed.

10. An apparatus in accordance with claim 1 characterized in that said apparatus further comprises:

light receiving means for receiving light rays transmitted through said object sample under test at a transmission angle relative to said object sample surface; and detection means within said densitometer connected to said light receiving means for detecting said light rays transmitted through said object sample surface and for generating electrical signals representative of spectral characteristics of said object sample surface.

11. An apparatus in accordance with claim 1 characterized in that said apparatus further comprises:

means for detecting an abnormal operating condition;

means responsive to said detection of said abnormal operating condition for storing data within said memory structure indicative of said abnormal operating conditions; and means for transmitting said stored data representative of said abnormal operating condition through said primary port means to said host system.

12. An apparatus in accordance with claim 1 characterized in that said apparatus further comprises:

display means for displaying information to a user of said densitometer apparatus; and means for transmitting data stored within said memory structure to said display means.

* * * * *

UNITED STATES PATENT AND TRADEMARK OFFICE
CERTIFICATE OF CORRECTION

PATENT NO. : 5,402,361
DATED : March 28, 1995
INVENTOR(S) : Steven H. Peterson et al.

It is certified that error appears in the above-identified patent and that said Letters Patent is hereby corrected as shown below:

Column 42, claim 1, line 37:
    delete "fur" and insert --for--

Column 43, claim 3, line 14:
    after "said" delete "primary".

Signed and Sealed this

Sixth Day of June, 1995

Attest:

BRUCE LEHMAN

*Attesting Officer*     *Commissioner of Patents and Trademarks*